(12) United States Patent
Wilkinson et al.

(10) Patent No.: US 7,897,608 B2
(45) Date of Patent: Mar. 1, 2011

(54) 39-DESMETHOXY-39-METHYL DERIVATIVES OF RAPAMYCIN

(75) Inventors: Barrie Wilkinson, Walden (GB); Mingqiang Zhang, Walden (GB); Rose Mary Sheridan, Walden (GB)

(73) Assignee: Biotica Technology Limited, Essex (GB)

( * ) Notice: Subject to any disclaimer, the term of this patent is extended or adjusted under 35 U.S.C. 154(b) by 191 days.

(21) Appl. No.: 12/273,917

(22) Filed: Nov. 19, 2008

(65) Prior Publication Data

US 2009/0176819 A1 Jul. 9, 2009

Related U.S. Application Data

(63) Continuation of application No. PCT/GB2007/001875, filed on May 18, 2007.

(30) Foreign Application Priority Data

May 19, 2006 (GB) ................................. 0609963.4

(51) Int. Cl.
C07D 498/18 (2006.01)
A61K 31/436 (2006.01)
(52) U.S. Cl. ...................................... 514/291; 540/456
(58) Field of Classification Search .................. 540/456; 514/291
See application file for complete search history.

(56) References Cited

U.S. PATENT DOCUMENTS

| | | |
|---|---|---|
| 3,929,992 A | 12/1975 | Sehgal |
| 5,023,262 A | 6/1991 | Caufield |
| 5,138,051 A | 8/1992 | Hughes |
| 5,221,670 A | 6/1993 | Caufield |
| 5,362,718 A | 11/1994 | Skotnicki |
| 5,378,836 A | 1/1995 | Kao |
| 5,391,730 A | 2/1995 | Skotnicki |
| 5,432,183 A | 7/1995 | Schulte |
| 5,446,048 A | 8/1995 | Failli |
| 5,563,145 A | 10/1996 | Failli |
| 5,665,772 A | 9/1997 | Cottens |
| 5,728,710 A | 3/1998 | Luengo |
| 5,912,253 A | 6/1999 | Cottens |
| 5,955,457 A | 9/1999 | Lee |
| 6,015,815 A | 1/2000 | Mollison |

FOREIGN PATENT DOCUMENTS

| | | |
|---|---|---|
| WO | WO 2003/064383 | 8/2003 |
| WO | WO 2004/007709 | 1/2004 |
| WO | WO 2004/101583 | 11/2004 |
| WO | WO 2006/095185 | 9/2006 |

OTHER PUBLICATIONS

Alarcon, C.M., Heitman, J., and Cardenas, M.E. (1999) Protein kinase activity and identification of a toxic effector domain of the target of rapamycin TOR proteins in yeast. *Molecular Biology of the Cell* 10: 2531-2546.
Aparicio, J.F., Molnár, I., Schwecke, T., König, A., Haydock, S.F., Khaw, L.E., Staunton, J., and Leadlay, P.F. (1996) Organization of the biosynthetic gene cluster for rapamycin in *Streptomyces hygroscopicus*: analysis of the enzymatic domains in the modular polyketide synthase. *Gene* 169: 9-16.
Baker, H., Sidorowicz, A., Sehgal, S.N., and Vézina, C. (1978) Rapamycin (AY-22,989), a new antifungal antibiotic. III. In vitro and in vivo evaluation. *Journal of Antibiotics* 31: 539-545.
Boulay, A., Zumstein-Mecker, S., Stephan, C., Beuvink, I., Zilbermann, F., Haller, R., Tobler, S., Heusser, C., O'Reilly, T., Stolz, B., Marti, A., Thomas, G., Lane, H.A.,. 2004, Antitumor efficacy of intermittent treatment schedules with the rapamycin derivative RAD001 correlates with prolonged inactivation of ribosomal protein S6 kinase 1 in peripheral blood mononuclear cells. *Cancer Res.* 64(1), 252-61.
Brown, E.J., Albers, M.W., Shin, T.B., Ichikawa, K., Keith, C.T., Lane, W.S., and Schreiber, S.L. (1994) A mammalian protein targeted by G1-arresting rapamycin-receptor complex. *Nature* 369: 756-758.
Brunn, G.J., Williams, J., Sabers, C., Wiederrecht, G., Lawrence, J.C., and Abraham, R.T. (1996) Direct inhibition of the signaling functions of the mammalian target of rapamycin by the phosphoinositide 3-kinase inhibitors, wortmannin and LY294002. *EMBO Journal* 15: 5256-5267.
Carlson, R.P., Hartman, D.A., Tomchek, L.A., Walter, T.L., Lugay, J.R., Calhoun, W., Sehgal, S.N., Chang, J.Y. (1993). Rapamycin, a potential disease-modifying antiarthritic drug. J. Pharmacol. Exp. Ther. 266(2):1125-38.
Crowe A, Bruelisauer A, Duerr L, Guntz P, Lemaire M. (1999) Absorption and intestinal metabolism of SDZ-RAD and rapamycin in rats. *Drug Metab Dispos*, 27(5), 627-32.
Dengler W.A., Schulte J., Berger D.P., Mertelsmann R. and Fiebig HH. (1995) Development of a propidium iodide fluorescence assay for proliferation and cytotoxicity assay. *Anti-Cancer Drugs*, 6:522-532.
DiLella, A.G., and Craig, R. J. (1991) Exon organization of the human FKBP-12 gene: correlation with structural and functional protein domains. *Biochemistry* 30: 8512- 8517.
Dudkin, L., Dilling, M.B., Cheshire, P.J., Harwood, F.C., Hollingshead, M., Arbuck, S.G., Travis, R., Sausville, E.A., Houghton, P.J. (2001). Biochemical correlates of mTOR inhibition by the rapamycin ester CCI-779 and tumor growth inhibition. Clin. Cancer Res. 7(6):1758-64.

(Continued)

*Primary Examiner*—Bruck Kifle

(57) ABSTRACT

The present invention relates to novel 39-desmethoxy-39-methylrapamycin derivatives, methods for their production, and uses thereof. In a further aspect the present invention provides for the use of these 39-desmethoxy-39-methylrapamycin derivatives in the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

39 Claims, 1 Drawing Sheet

OTHER PUBLICATIONS

Evans D.A., Gage J.R. and Leighton J.L. (1992) Assymetric synthesis of calyculin A. 3. Assemblage of the calyculin skeleton and the introduction of a new phosphate monoester synthesis. *J. Org. Chem.*, 57:1964-1966.

Fiebig H.H., Dengler W.A. and Roth T. (1999) Human tumor xenografts: Predictivity, characterization, and discovery of new anticancer agents. In: Fiebig HH, Burger AM (eds). Relevance of Tumor Models for Anticancer Drug Development. *Contrib. Oncol.*, 54: 29-50.

Findlay J.A, and Radics, L. (1980) *Canadian Journal of Chemistry* 58:579.

Fishbein, T.M., Florman, S., Gondolesi, G., Schiano, T., LeLeiko, N., Tschernia, A., Kaufman, S. (2002). Intestinal transplantation before and after the introduction of sirolimus. *Transplantation*. 73(10):1538-42.

Foey, A., Green, P., Foxwell, B., Feldmann, M., Brennan, F. (2002). Cytokine-stimulated T cells induce macrophage IL-10 production dependent on phosphatidylinositol 3-kinase and p70S6K: implications for rheumatoid arthritis. *Arthritis Res.* 4(1):64-70. Epub 2001 Oct. 10.

Furniss B.S., Hannaford A.J., Smith P.W.G. and Tatchell A.R. (1989) *Vogel's textbook of practical organic chemistry*, 5th Ed, Pearson, Prentice Hall, Harlow, UK.

Gallant-Haidner HL, Trepanier DJ, Freitag DG, Yatscoff RW. 2000, "Pharmacokinetics and metabolism of sirolimus". *Ther Drug Monit.* 22(1), 31-5.

Gregory, C.R., Huie, P., Billingham, M.E. and Morris, R.E. (1993). Rapamycin inhibits arterial intimal thickening caused by both alloimmune and mechanical injury. Its effect on cellular, growth factor and cytokine response in injured vessels. *Transplantation* 55(6): 1409-1418.

Gregory MA, Gaisser S, Lill RE, Hong H, Sheridan RM, Wilkinson B, Petkovic H, Weston AJ, Carletti I, Lee HL, Staunton J, Leadlay PF. (2004) "Isolation and characterization of pre-rapamycin, the first macrocyclic intermediate in the biosynthesis of the immunosuppressant rapamycin by S. hygroscopicus". *Angew Chem Int Ed Engl.* 43(19), 2551-3.

Gu, J, Ruppen ME, Cai P. (2005), Lipase-Catalyzed Regioselective Esterification of Rapamycin: Synthesis of Temsirolimus (CCI-779). Org. Lett. 7(18): 3945-3948.

Guba, M., von Breitenbuch, P., Steinbauer, M., Koehl, G., Flegel, S., Hornung, M., Bruns, C.J., Zuelke, C., Farkas, S., Anthuber, M., Jauch, K.W., and Geissler, E.K. (2002) Rapamycin inhibits primary and metastatic tumor growth by antiangiogenesis: involvement of vascular endothelial growth factor. *Nature Medicine* 8: 128-135.

Hardwick, J.S., Kuruvilla, F.G., Tong, J.K., Shamji, A.F., and Schreiber, S.L. (1999) Rapamycin-modulated transcription defines the subset of nutrient-sensitive signaling pathways directly controlled by the Tor proteins. *Proceedings of the National Academy of Sciences of the United States of America* 96: 14866-14870.

Hentges, K.E., Sirry, B., Gingeras, A.C., Sarbassov, D., Sonenberg, N., Sabatini, D., and Peterson, A.S. (2001) FRAP/mTOR is required for proliferation and patterning during embryonic development in the mouse. *Proceedings of the National Academy of Sciences of the United States of America* 98: 13796-13801.

Jain, S., Bicknell, G.R., Whiting, P.H., Nicholson, M.L. (2001). Rapamycin reduces expression of fibrosis-associated genes in an experimental model of renal ischaemia reperfusion injury. *Transplant Proc.* 33(1-2):556-8.

Kahan, B.D., and Camardo, J.S. (2001) Rapamycin: Clinical results and future opportunities.*Transplantation* 72:1181-1193.

Kahan, B.D., Chang, J.Y., and Sehgal, S.N. (1991) Preclinical evaluation of a new potent immunosuppressive agent, rapamycin. *Transplantation* 52: 185-191.

Kirby, B., and Griffiths,C.E.M. (2001) Psoriasis: the future. *British Journal of Dermatology* 144:37-43.

Kirchner, G.I., Winkler, M., Mueller L., Vidal, C., Jacobsen, W., Franzke, A., Wagner, S., Blick, S., Manns M.P., and Sewing K.-F. (2000) Pharmacokinetics of SDZ RAD and cyclosporin including their metabolites in seven kidney graft patients after the first dose of SDZ RAD. British Journal of Clinical Pharmacology 50:449-454.

Kuo, C.J., Chung, J.K., Fiorentino, D.F., Flanagan, W.M., Blenis, J., and Crabtree, G.R. (1992) Rapamycin selectively inhibits interleukin-2 activation of p70 S6 kinase. *Nature* 358: 70-73.

Li, A.P. (1992) Screening for human ADME/Tox drug properties in drug discovery. *Drug Discovery Today*, 6, 357-366.

Lyons, W.E., George, E.B., Dawson, T.M., Steiner, J.P., and Snyder, S.H. (1994) Immunosuppressant FK506 promotes neurite outgrowth in cultures of PC12 cells and sensory ganglia. *Proceedings of the National Academy of Sciences of the United States of America* 91:3191-3195.

McAlpine, J. B,.Swanson S. J., Jackson, M., Whittern, D.N. (1991). Revised NMR assignments for rapamycin. *Journal of Antibiotics* 44: 688-690.

Morice, M.C., Serruys, P.W., Sousa, J.E., Fajadet, J., Ban Hayashi, E., Perin, M., Colombo, A., Schuler, G., Barragan, P., Guagliumi, G., Molnar, F., Falotico, R. (2002). RAVEL Study Group. Randomized Study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization. *N. Eng.l J. Med.* 346(23):1773-80.

Myckatyn, T.M., Ellis, R.A., Grand, A.G., Sen, S.K., Lowe, J.B. 3rd, Hunter, D.A., Mackinnon, S.E. (2002). The effects of rapamycin in murine peripheral nerve isografts and allografts. *Plast. Reconstr. Surg.* 109(7):2405-17.

Navé, B.T., Ouwens, D.M., Withers, D.J., Alessi, D.R., and Sheperd, P.R. (1999) Mammalian target of rapamycin is a direct target for protein kinase B: identification of a convergence point for opposing effects of insulin and amino-acid deficiency on protein translation. *Biochemical Journal* 344:427-431.

Paiva, N.L., Demain, A.L., and Roberts, M.F. (1991) Incorporation of acetate, propionate, and methionine into rapamycin by *Streptomyces hygroscopicus. Journal of Natural Products* 54: 167-177.

Paiva, N. L., Demain, A.L., and Roberts, M.F. (1993) The immediate precursor of the nitrogen-containing ring of rapamycin is free pipecolic acid. *Enzyme and Microbial Technology* 15: 581-585.

Perin, E C, (2005), "Choosing a Drug-Eluting Stent: A Comparison Between CYPHER and TAXUS", *Reviews in Cardiovascular Medicine*, 6 (suppl 1), pp. S13-S21.

Powell, N., Till, S., Bungre, J., Corrigan, C. (2001). The immunomodulatory drugs cyclosporin A, mycophenolate mofetil, and sirolimus (rapamycin) inhibit allergen-induced proliferation and IL-5 production by PBMCs from atopic asthmatic patients.*J. Allergy Clin. Immunol.* 108(6):915-7.

Rabinovitch, A., Suarez-Pinzon, W.L., Shapiro, A.M., Rajotte, R.V., Power, R. (2002). Combination therapy with sirolimus and interleukin-2 prevents spontaneous and recurrent autoimmune diabetes in NOD mice.Diabetes. 51(3):638-45.

Raught, B., Gingras, A.C., and Sonenberg, N. (2001) The target of rapamycin (TOR) proteins. *Proceedings of the National Academy of Sciences of the United States of America* 98: 7037-7044.

Reather, J. A., (2000), Ph.D. Dissertation, University of Cambridge. "Late steps in the biosynthesis of macrocyclic lactones".

Reitamo, S., Spuls, P., Sassolas, B., Lahfa, M., Claudy, A., Griffith, C.E.; Sirolimus European Psoriasis Study Group. (2001). Efficacy of sirolimus (rapamycin) administered concomitantly with a subtherapeutic dose of cyclosporin in the treatment of severe psoriasis: a randomized controlled trial. *Br. J. Dermatol.* 145(3):438-45.

Roth T., Burger A.M., Dengler W., Willmann H. and Fiebig H.H. (1999) Human tumor cell lines demonstrating the characteristics of patient tumors as useful models for anticancer drug screening. In: Fiebig HH, Burger AM (eds). Relevance of Tumor Models for Anticancer Drug Development. *Contrib. Oncol.*, 54: 145-156.

Roymans, D., and Slegers, H. (2001) Phosphaditidylinositol 3-kinases in tumor progression. *European Journal of Biochemistry* 268:487-498.

Schwecke, T., Aparicio, J.F., Molnár, I., König, A., Khaw, L.E., Haydock, S.F., Oliynyk, M., Caffrey, P., Cortés, J., Lester, J.B., Böhm, G.A., Staunton, J., and Leadlay, P.F. (1995) The biosynthetic gene cluster for the polyketide immunosuppressant rapamycin. *Proceedings of the National Academy of Sciences of the United States of America* 92: 7839-7843.

Sedrani, R., Cottens, S., Kallen, J., and Schuler, W. (1998) Chemical modifications of rapamycin: the discovery of SDZ RAD. *Transplantation Proceedings* 30: 2192-2194.

Sehga, S.N., Baker, H., and Vézina, C. (1975) Rapamycin (AY-22,989), a new antifungal antibiotic II. Fermentation, isolation and characterization. *The Journal of Antibiotics* 28: 727-733.

Shepherd, P.R., Withers, D.J., and Siddle K. (1998) Phosphoinositide 3-kinase: the key switch mechanism in insulin signalling. *Biochemical Journal* 333: 471-490.

Smith M.B. and March J. (2001) *March's advanced organic Chemistry*, 5th Ed, John Wiley and Sons Inc., UK.

Steiner, J.P., Hamilton, G.S., Ross, D. T., Valentine, H.L., Guo, H., Connolly, M.A., Liang, S., Ramsey, C., Li, J.-H.J., Huang, W., Howorth, P., Soni, R., Fuller, M., Sauer, H., Nowotnik, A.C., and Suzdak, P.D. (1997) Neutrophic immunophilin ligands stimulate structural and functional recovery in neurodegenerative animal models. *Proceedings of the National Academy of Sciences of the United States of America* 94:2019-2024.

Tang, S.J., Reis, G., Kang, H., Gingras, A.-C., Sonenberg, N., and Schuman, E.M. (2002) A rapamycin-sensitive signaling pathway contributes to long-term synaptic plasticity in the hippocampus. *Proceedings of the National Academy of Sciences of the United States of America* 1:467-472.

Toshima K. and Tatsuta K. (1993) Recent progress in *O*-glycosylation methods and its application to natural product synthesis. *Chem. Rev.*, 93:1503-1531.

Trepanier DJ, Gallant H, Legatt DF, Yatscoff RW. (1998), "Rapamycin: distribution, pharmacokinetics and therapeutic range investigations: an update". *Clin Biochem*. 31(5):345-51.

Vézina, C., Kudelski, A., and Sehgal, S.N. (1975) Rapamycin (AY-22,989), a new antifungal antibiotic. I. Taxonomy of the producing streptomycete and isolation of the active principle. *The Journal of Antibiotics* 28: 721-726.

Volpe, D.A., Faustino, P.J., Yu, L.X., (2001) Towards standardisation of an in vitro method of drug absorption. *Pharmacopeial Forum*, 27, 2916-2922.

Waller, J.R., and Nicholson, M.L. (2001) Molecular mechanisms of renal allograft fibrosis. *British Journal of Surgery* 88:1429-1441.

Warner, L.M., Adams, L.M., Chang, J.Y., Sehgal, S.N. (1992). A modification of the in vivo mixed lymphocyte reaction and rapamycin's effect in this model.Clin. Immunol. Immunopathol. 64(3):242-7.

Yu, K., Toral-Barza, L., Discafani, C., Zhang, W.G., Skotnicki, J., Frost, P., Gibbons, J.J. (2001) mTOR, a novel target in breast cancer: the effect of CCI-779, an mTOR inhibitor, in preclinical models of breast cancer. Endocrine-Related Cancer 8:249-258.

Zhu, J., Wu 3., Frizell, E., Liu, S.L., Bashey, R., Rubin, R., Norton, P., Zern, M.A. (1999). Rapamycin inhibits hepatic stellate cell proliferation in vitro and limits fibrogenesis in an in vivo model of liver fibrosis. *Gastroenterology*. 117(5):1198-204.

39-DESMETHOXY-39-METHYL DERIVATIVES OF RAPAMYCIN

CROSS-REFERENCE TO RELATED APPLICATIONS

This application is a continuation of International Patent Application No. PCT/GB2007/001875, filed May 18, 2007.

The present invention relates to novel 39-desmethoxy-39-methylrapamycin derivatives, methods for their production, and uses thereof. In a further aspect the present invention provides for the use of these 39-desmethoxy-39-methylrapamycin derivatives in the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

Rapamycin (sirolimus) (FIG. 1) is a lipophilic macrolide produced by *Streptomyces hygroscopicus* NRRL 5491 (Sehgal et al., 1975; Vézina et al., 1975; U.S. Pat. Nos. 3,929,992; 3,993,749) with a 1,2,3-tricarbonyl moiety linked to a pipecolic acid lactone (Paiva et al., 1991). For the purpose of this invention rapamycin is described by the numbering convention of McAlpine et al. (1991) in preference to the numbering conventions of Findlay et al. (1980) or Chemical Abstracts (11$^{th}$ Cumulative Index, 1982-1986 p 60719CS).

Rapamycin has significant pharmacological value due to the wide spectrum of activities exhibited by the compound. Rapamycin shows moderate antifungal activity, mainly against *Candida* species but also against filamentous fungi (Baker et al., 1978; Sehgal et al., 1975; Vézina et al., 1975; U.S. Pat. Nos. 3,929,992; 3,993,749). Rapamycin inhibits cell proliferation by targeting signal transduction pathways in a variety of cell types, e.g. by inhibiting signalling pathways that allow progression from the G$_1$ to the S-phase of the cell cycle (Kuo et al., 1992). In T cells rapamycin inhibits signalling from the IL-2 receptor and subsequent autoproliferation of the T cells resulting in immunosuppression. The inhibitory effects of rapamycin are not limited to T cells, since rapamycin inhibits the proliferation of many mammalian cell types (Brunn et al., 1996). Rapamycin is, therefore, a potent immunosuppressant with established or predicted therapeutic applications in the prevention of organ allograft rejection and in the treatment of autoimmune diseases (Kahan et al., 1991). 40-O-(2-hydroxy)ethyl -rapamycin (SDZ RAD, RAD 001, Certican, everolimus) is a semi-synthetic analogue of rapamycin that shows immunosuppressive pharmacological effects and is also under investigation as an anticancer agent (Sedrani, R. et al., 1998; Kirchner et al., 2000; U.S. Pat. No. 5,665,772, Boulay et al, 2004). Approval for this drug as an immunosuppressant was obtained for Europe in 2003. The rapamycin ester derivative CCI-779 (Wyeth-Ayerst) inhibits cell growth in vitro and inhibits tumour growth in vivo (Yu et al., 2001). CCI-779 is currently in Phase III clinical trials as a potential anti-cancer agent. The value of rapamycin in the treatment of chronic plaque psoriasis (Kirby and Griffiths, 2001), the potential use of effects such as the stimulation of neurite outgrowth in PC12 cells (Lyons et al., 1994), the block of the proliferative responses to cytokines by vascular and smooth muscle cells after mechanical injury (Gregory et al., 1993) and its role in prevention of allograft fibrosis (Waller and Nicholson, 2001) are areas of intense research (Kahan and Camardo, 2001). Recent reports reveal that rapamycin is associated with a lower incidence of cancer in organ allograft patients on long-term immunosuppressive therapy than those on other immunosuppressive regimes, and that this reduced cancer incidence is due to inhibition of angiogenesis (Guba et al., 2002). It has been reported that the neurotrophic activities of immunophilin ligands are independent of their immunosuppressive activity (Steiner et al., 1997) and that nerve growth stimulation is promoted by disruption of the mature steroid receptor complex as outlined in the patent application WO 01/03692. Side effects such as hyperlipidemia and thrombocytopenia as well as potential teratogenic effects have been reported (Hentges et al., 2001; Kahan and Camardo, 2001).

The polyketide backbone of rapamycin is synthesised by head-to-tail condensation of a total of seven propionate and seven acetate units to a shikimate derived cyclohexanecarboxylic acid starter unit by the very large, multifunctional proteins that comprise the Type I polyketide synthase (rap PKS, Paiva et al., 1991). The L-lysine derived amino acid, pipecolic acid, is condensed via an amide linkage onto the last acetate of the polyketide backbone (Paiva et al., 1993) and is followed by lactonization to form the macrocycle.

The nucleotide sequences for each of the three rapamycin PKS genes, the NRPS-encoding gene and the flanking late gene sequences and the corresponding polypeptides, were identified by Aparicio et al., 1996, and Schwecke et al., 1995 and were deposited with the NCBI under accession number X86780, and corrections to this sequence have recently been published in WO 04/007709.

The first enzyme-free product of the rapamycin biosynthetic cluster has been designated pre-rapamycin (WO 04/007709, Gregory et al., 2004). Production of the fully processed rapamycin requires additional processing of the polyketide/NRPS core by the enzymes encoded by the rapamycin late genes, RapJ, RapN, RapO, RapM, RapQ and RapI.

The pharmacologic actions of rapamycin characterised to date are believed to be mediated by the interaction with cytosolic receptors termed FKBPs. The major intracellular rapamycin receptor in eukaryotic T-cells is FKBP12 (DiLella and Craig, 1991) and the resulting complex interacts specifically with target proteins to inhibit the signal transduction cascade of the cell.

The target of the rapamycin-FKBP12 complex has been identified in yeast as TOR (target of rapamycin) (Alarcon et al., 1999) and the mammalian protein is known as FRAP (FKBP-rapamycin associated protein) or mTOR (mammalian target of rapamycin) (Brown et al., 1994).

A link between mTOR signalling and localized protein synthesis in neurons; its effect on the phosphorylation state of proteins involved in translational control; the abundance of components of the translation machinery at the transcriptional and translational levels; control of amino acid permease activity and the coordination of the transcription of many enzymes involved in metabolic pathways have been described (Raught et al., 2001). Rapamycin sensitive signalling pathways also appear to play an important role in embryonic brain development, learning and memory formation (Tang et al., 2002). Research on TOR proteins in yeast also revealed their roles in modulating nutrient-sensitive signalling pathways (Hardwick et al., 1999). Similarly, mTOR has been identified as a direct target for the action of protein kinase B (akt) and of having a key role in insulin signalling (Shepherd et al., 1998; Navé et al., 1999). Mammalian TOR has also been implicated in the polarization of the actin cytoskeleton and the regulation of translational initiation (Alarcon et al., 1999). Phosphatidylinositol 3-kinases, such as mTOR, are functional in several aspects of the pathogenesis of tumours such as cell-cycle progression, adhesion, cell survival and angiogenesis (Roymans and Slegers, 2001).

Pharmacokinetic studies of rapamycin and rapamycin analogues have demonstrated the need for the development of novel rapamycin compounds that may be more stable in solution, more resistant to metabolic attack and/or have improved cell membrane permeability and decreased efflux and which therefore may exhibit improved oral bio-availability.

A range of synthesised rapamycin analogues using the chemically available sites of the molecule has been reported. The description of the following compounds was adapted to the numbering system of the rapamycin molecule described in FIG. 1. Chemically available sites on the molecule for derivatization or replacement include C40 and C28 hydroxyl groups (e.g. U.S. Pat. Nos. 5,665,772; 5,362,718), C39 and C16 methoxy groups (e.g. WO 96/41807; U.S. Pat. No. 5,728, 710), C32, C26 and C9 keto groups (e.g. U.S. Pat. Nos. 5,378,836; 5,138,051; 5,665,772). Hydrogenation at C17, C19 and/or C21, targeting the triene, resulted in retention of antifungal activity but relative loss of immunosuppression (e.g. U.S. Pat. Nos. 5,391,730; 5,023,262). Significant improvements in the stability of the molecule (e.g. formation of oximes at C32, C40 and/or C28, U.S. Pat. Nos. 5,563,145, 5,446,048), resistance to metabolic attack (e.g. U.S. Pat. No. 5,912,253), bioavailability (e.g. U.S. Pat. Nos. 5,221,670; 5,955,457; WO 98/04279) and the production of prodrugs (e.g. U.S. Pat. Nos. 6,015,815; 5,432,183) have been achieved through derivatization.

However, there remains a need for a greater range of rapamycin derivatives. Such rapamycin derivatives would have great utility in the treatment of a wide range of conditions. The present invention provides a range of novel 39-desmethoxy-39-methylrapamycin derivatives. Such compounds are useful in medicine, in particular for the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections.

The present invention provides 39-desmethoxy-39-methyl derivatives of rapamycin, methods for the preparation of these compounds, intermediates thereto and methods for the use of these compounds in medicine.

In its broadest aspect the present invention provides 39-desmethoxy-39-methyl derivatives of rapamycin characterised in that the 40-hydroxy position is derivatized as a carboxylic acid ester, as an ether, as a phosphinate ester, as an acetal or as a glycosyl.

When 39-desmethoxy-39-methylrapamycin is derivatized as a carboxylic acid ester, as an ether or as an acetal the derivatizing group preferably contains no more than 12 carbon atoms (especially 7 or fewer particularly 5 or fewer carbon atoms). Preferably it contains at least one functional group (especially at least two functional groups) selected from —$CF_2PO(OH)_2$, —$PO(OH)_2$, —COOH, —OH and —$NH_2$ particularly selected from —COOH and —OH more particularly —OH.

When 39-desmethoxy-39-methylrapamycin is derivatized as an acetal derived from a glycosyl group preferably each glycosyl is formed from a sugar or a glycoside which preferably contains no more than 12 carbon atoms (especially 7 or fewer, particularly 6 or fewer carbon atoms). Examples include mono and disaccharides, particularly monosaccharides which form 5- and 6-membered rings. Preferably it contains at least one functional group (especially at least two function groups) selected from —COOH, —OH and —$NH_2$ particularly selected from —$NH_2$ and —OH more particularly —OH.

When 39-desmethoxy-39-methylrapamcyin is derivatized as a phosphinate ester preferably the alkyl groups preferably contain no more than 4 carbon atoms, an example is the ester formed with phosphinic acid.

Specific examples of derivatizing moieties are given below.

In a more specific aspect the present invention provides 39-desmethoxy-39-methylrapamycin derivatives according to formula (I) below, or a pharmaceutically acceptable salt thereof:

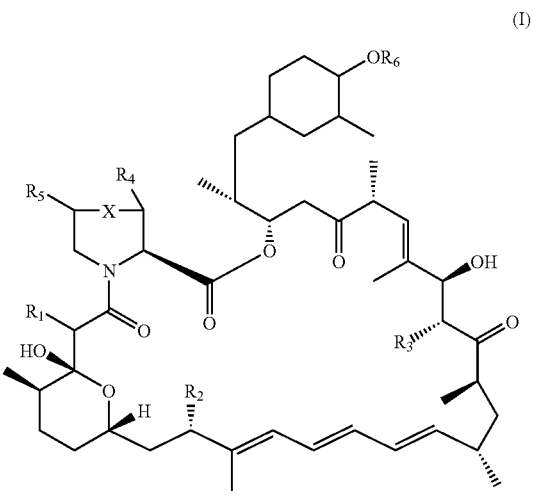

(I)

wherein:
X represents bond or $CH_2$;
$R_1$ represents a keto group or (H,H);
$R_2$ represents OH or OMe;
$R_3$ represents H, OH or OMe;
$R_4$ and $R_5$ each independently represent H or OH;
$R_6$ represents —$R_7$, —$C(O)R_7$, —$POR_{19}R_{20}$, or Y—$R_{15}$;
$R_7$ represents —$(CR_8R_9)_m(CR_{10}R_{11})_pCR_{12}R_{13}R_{14}$;
$R_8$ and $R_9$ each independently represent C1-C4 alkyl, C2-C4 alkenyl or C2-C4 alkynyl, any of which groups may optionally be substituted with —$PO(OH)_2$, —$CF_2PO(OH)_2$, —OH, —COOH or —$NH_2$; or $R_8$ and $R_9$ each independently represent H, trifluoromethyl or F;
$R_{10}$, $R_{11}$, $R_{12}$, $R_{13}$ and $R_{14}$ each independently represent C1-C4 alkyl, C2-C4 alkenyl or C2-C4 alkynyl, any of which groups may optionally be substituted with —$PO(OH)_2$, —$CF_2PO(OH)_2$, —OH, —COOH or —$NH_2$; or $R_{10}$, $R_{11}$, $R_{12}$, $R_{13}$ and $R_{14}$ may be independently selected from H, —$(CR_8R_9)_qNH_2$, —$(CR_8R_9)_qOH$, $CF_3$, F, COOH; or $R_{10}$ and $R_{11}$ or $R_{12}$ and $R_{13}$ or $R_{13}$ and $R_{14}$ may be taken together with the carbon to which they are joined to form a C3-C6 cycloalkyl or a 3- to 6-membered heteroalkyl ring that contains one or more heteroatoms selected from N, O and S and that is optionally, substituted with up to 5-$(CR_8R_9)_qOH$, —$(CR_8R_9)_qNH_2$ or COOH groups;
Y=bond, —C(O)—O—; —$(CH_2)_2$—O—C(O)—O—;
$R_{15}$ represents

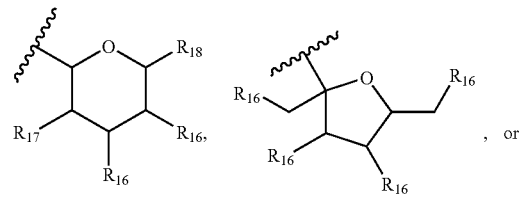

-continued

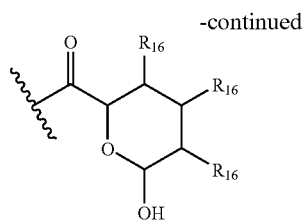

$R_{16}$ are each independently H or OH;
$R_{17}$ is independently selected from H, OH and $NH_2$;
$R_{18}$ is independently selected from H, $-CH_3$, $-CH_2OH$ and $-COOH$;
provided however that no more than 2 groups selected from $R_{16}$, $R_{17}$ and $R_{18}$ represent H or $CH_3$;
$R_{19}$ and $R_{20}$ each independently represent H or C1-C4 alkyl;
m, p and q each independently represent an integer between 0-4;
provided the $R_7$ moiety does not contain more than 12 carbon atoms and does contain at least one functional group selected from $-PO(OH)_2$, $-CF_2PO(OH)_2$, $-COOH$, OH or $NH_2$; or a pharmaceutically acceptable salt thereof.

The above structure shows a representative tautomer and the invention embraces all tautomers of the compounds of formula (I) for example keto compounds where enol compounds are illustrated and vice versa.

Unless particular stereoisomers are specifically indicated (e.g. by a bolded or dashed bond at a relevant stereocentre in a structural formula, by depiction of a double bond as having E or Z configuration in a structural formula, or by using stereochemistry-designating nomenclature), all stereoisomers are included within the scope of the invention as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates and hydrates are also encompassed within the scope of this invention.

In a further aspect, the present invention provides 39-desmethoxy-39-methylrapamycin derivatives such as compounds of formula (I) or a pharmaceutically acceptable salt thereof, for use as a pharmaceutical.

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

In particular, the term "39-desmethoxy-39-methylrapamycin analogue" refers to a 39-desmethoxy-39-methylrapamycin compound produced by the methods of WO 2004/007709 and as shown by formula (II). These compounds are also referred to as "parent compounds" and these terms are used interchangeably in the present application. In the present application the term "39-desmethoxy-39-methylrapamycin analogues" includes reference to 39-desmethoxy-39-methylrapamycin itself.

As used herein the term "derivative(s)" refers to chemical compounds that have been modified from their parent compound by semi-synthetic organic chemistry.

In particular, the term "39-desmethoxy-39-methylrapamycin derivative" refers to a 39-desmethoxy-39-methylrapamycin derivative according to formula (I) above, or a pharmaceutically acceptable salt thereof, produced by semisynthetic alteration of a 39-desmethoxy-39-methylrapamycin analogue. These compounds are also referred to as "compounds of the invention" or "39-desmethoxy-39-methyl derivatives of rapamycin" and these terms are used interchangeably in the present application.

As used herein, the term "autoimmune disorder(s)" relates to conditions wherein an adaptive immune response is mounted against self-antigens which are typically characterised by chronic inflammatory injury to tissues. Autoimmune disorders included within the scope of the invention but not limited to, are: systemic lupus erythrematosis (SLE), rheumatoid arthritis, myasthenia gravis, insulin-dependent diabetes mellitus and multiple sclerosis.

As used herein, the term "diseases of inflammation" includes conditions wherein the inflammatory system overreacts to cause tissue injury and/or unnecessary side-effects. The over-reaction may be to a non-self antigen, a self antigen or may occur spontaneously. Inflammatory disease includes allergies (also known as hypersensitivity reactions). Examples of diseases of inflammation include but are not limited to: psoriasis, dermatitis, eczema, seborrhoea, inflammatory bowel disease (including but not limited to ulcerative colitis and Crohn's disease), pulmonary inflammation (including asthma, chronic obstructive pulmonary disease, emphysema, acute respiratory distress syndrome and bronchitis), rheumatoid arthritis and eye uveitis.

As used herein, the term "cancer" refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumor cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer and ovarian cancer.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein, the term "vascular disease" includes, without limitation: hyperproliferative vascular disorders (e.g. restenosis and vascular occlusion), graft vascular atherosclerosis, cardiovascular disease, cerebral vascular disease and peripheral vascular disease (e.g. coronary artery disease, arteriosclerosis, atherosclerosis, nonatheromatous arteriosclerosis or vascular wall damage).

As used herein the terms "neuronal regeneration" refers to the stimulation of neuronal cell growth and includes neurite outgrowth and functional recovery of neuronal cells. Diseases and disorders where neuronal regeneration may be of significant therapeutic benefit include, but are not limited to, Alzheimer's disease, Parkinson's disease, Huntington's chorea, amyotrophic lateral sclerosis, trigeminal neuralgia, glossopharyngeal neuralgia, Bell's palsy, muscular dystrophy, stroke, progressive muscular atrophy, progressive bulbar inherited muscular atrophy, cervical spondylosis, Gullain-Barre syndrome, dementia, peripheral neuropathies and peripheral nerve damage, whether caused by physical injury (e.g. spinal cord injury or trauma, sciatic or facial nerve lesion or injury) or a disease state (e.g. diabetes).

As used herein the term "fibrotic diseases" refers to diseases associated with the excess production of the extracellular matrix and includes (without limitation) sarcoidosis, keloids, glomerulonephritis, end stage renal disease, liver fibrosis (including but not limited to cirrhosis, alcohol liver disease and steato-heptatitis), chronic graft nephropathy, surgical adhesions, vasculopathy, cardiac fibrosis, pulmonary fibrosis (including but not limited to idiopathic pulmonary fibrosis and cryptogenic fibrosing alveolitis), macular degeneration, retinal and vitreal retinopathy and chemotherapy or radiation-induced fibrosis.

As used herein, the term "graft vs. host disease" refers to a complication that is observed after allogeneic stem cell/bone marrow transplant. It occurs when infection-fighting cells from the donor recognize the patient's body as being different or foreign. These infection-fighting cells then attack tissues in the patient's body just as if they were attacking an infection. Graft vs. host disease is categorized as acute when it occurs within the first 100 days after transplantation and chronic if it occurs more than 100 days after transplantation. Tissues typically involved include the liver, gastrointestinal tract and skin. Chronic graft vs. host disease occurs approximately in 10-40 percent of patients after stem cell/bone marrow transplant.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

The term "water solubility" as used in this application refers to solubility in aqueous media, e.g. phosphate buffered saline (PBS) at pH 7.4.

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

Alkyl, alkenyl and alkynyl groups may be straight chain or branched.

Examples of C1-C4 alkyl groups include methyl, ethyl, n-propyl, i-propyl and n-butyl.

Examples of C2-C4 alkenyl groups include ethenyl and 2-propenyl.

Examples of C2-4 alkynyl groups include ethynyl.

C3-C6 cycloalkyl group refers to a cycloalkyl ring including 3-6 carbon atoms that may optionally be branched. Examples include cyclopropyl, cyclobutyl, methyl-cyclobutyl, cyclopentyl and cyclohexyl.

3- to 6-membered heteroalkyl rings containing one or more heteroatoms selected from N, O and S include rings containing one or two heteroatoms, especially one heteroatom. Examples include furan, pyran, oxetane, oxirane, piperidine, pyrrolidine, azetidine, aziridine, thiirane, thiethane, thiophene, thiopyran and morpholine.

Example optional substituents for the 3- to 6-membered heteroalkyl rings include —OH, —CH$_2$OH, NH$_2$, CH$_2$NH$_2$ and COOH. Typically the 3- to 6-membered heteroalkyl rings may be unsubstituted or substituted by 1 or 2, e.g. 1 substituent.

DESCRIPTION OF THE INVENTION

The present invention provides 39-desmethoxy-39-methylrapamycin derivatives, as set out above, methods for the preparation of these compounds, intermediates thereto and methods for the use of these compounds in medicine.

Preferably $R_7$ contains 7 or fewer especially 5 or fewer carbon atoms.

$R_7$ preferably contains at least one functional group selected from —PO(OH)$_2$, —OH, —COOH and —NH$_2$, more preferably —OH, —COOH or —NH$_2$ especially —COOH and OH, most especially OH. Preferably $R_7$ contains 2 or more substituents, e.g. 2—OH groups.

Suitably X represents CH$_2$;

Suitably p represents 0 or 1.

Suitably m represents 0 or 1.

Suitably q represents 0, 1 or 2.

Suitably $R_{11}$ represents H. Suitably $R_{12}$ represents H.

Suitably $R_{13}$ represents H or OH.

When p represents 1, suitably $R_{10}$ represents Me, OH or CH$_2$OH.

When p represents 1, suitably $R_{11}$ represents Me, H or CH$_2$OH.

When m and p both represent 0, suitably $R_{12}$ and $R_{13}$ both represent H, $R_{14}$ represents —(CR$_8$R$_9$)$_q$—OH where q=0 or 1 and $R_8$ and $R_9$ both represent H.

When p represents 1 and m represents 0, suitably $R_{10}$ and $R_{11}$ both represent H, $R_{12}$ represents H, $R_{13}$ represents H, OH or NH$_2$, $R_{14}$ represents —(CR$_8$R$_9$)$_q$—OH where q=0 or 1 and $R_8$ and $R_9$ both represent H.

When $R_6$ represents —POR$_{15}$R$_{16}$ suitably $R_{15}$ and $R_{16}$ both represent CH$_3$ or both represent CH$_2$CH$_3$.

Suitably $R_6$ represents the residue derived from forming an ester with hydroxyl acetic acid, 3-hydroxy-2,2-dimethylpropionic acid, 2,3-dihydroxypropionic acid, 3-hydroxy-2-hydroxymethylpropionic acid or 2,2-bis(hydroxymethyl)propionic acid.

In one example set of compounds, $R_6$ represents: C(O)R$_7$

Preferably $R_7$ is the moiety formed by condensation of the macrocyclic alcohol with an acid selected from the list consisting of hydroxyacetic acid, 3-hydroxy-2,2,dimethylpropionic acid, 2,3-dihydroxypropionic acid, 3-hydroxy-2-hydroxymethylpropionic acid and 2,2-bis(hydroxymethyl) propionic acid, especially 2,2-bis(hydroxymethyl)propionic acid.

When $R_{15}$ represents:

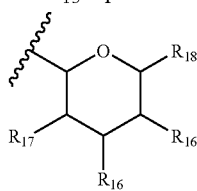

examples of this moiety include the moiety formed by forming an acetal with (i) glucose (i.e. $R_{18}$ represents $CH_2OH$ and each $R_{16}$ and $R_{17}$ represents OH), e.g. D-glucose (ii) glucosamine (i.e. $R_{18}$ represents $CH_2OH$, each $R_6$ represents OH and $R_{17}$ represents $NH_2$) e.g. D-glucosamine, (iii) glucuronic acid (i.e. $R_{18}$ represents COOH and each $R_{16}$ and $R_{17}$ represents OH) e.g. D-glucuronic acid and (iv) arabinose (i.e. $R_{18}$ represents H and each $R_{16}$ and $R_{17}$ represents OH) e.g. D-arabinose.

When $R_{15}$ represents:

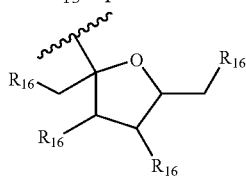

examples of this moiety include the moiety formed by forming an acetal with fructose (i.e. $R_{16}$ each represents OH), e.g. the residue of D-fructose.

When $R_{15}$ represents:

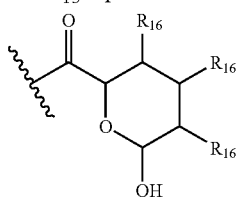

examples of this moiety include the moiety formed by forming an ester with glucuronic acid (i.e. each $R_{16}$ represents OH), e.g. the residue of D-glucuronic acid.

In general, the compounds of the invention are prepared by semi-synthetic derivatization of a 39-desmethoxy-39-methylrapamycin analogue of formula (II).

Thus a process for preparing a compound of formula (I) or a pharmaceutically acceptable salt thereof comprises:

(a) reacting a 39-desmethoxy-39-methylrapamycin analogue of formula (II):

(II)

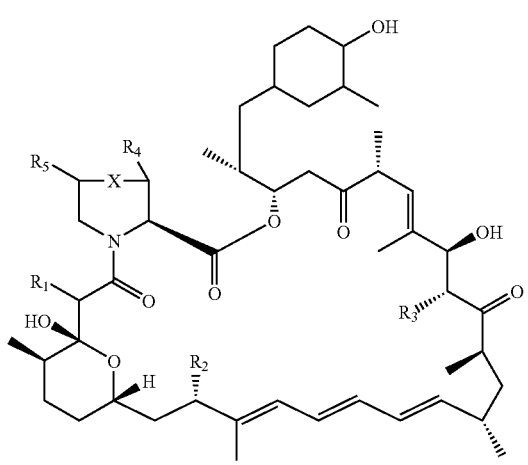

or a protected derivative thereof, with a compound of formula (III):

HO—$R_6$ (III)

or an activated derivative of $R_6$;

(b) converting a compound of formula (I) or a salt thereof to another compound of formula (I) or another pharmaceutically acceptable salt thereof; or (c) deprotecting a protected compound of formula (I).

The term "activated derivative" as used above refers to (for example but without limitation): in the case of esters—carboxylic acids, acyl halides, mixed anhydrides, symmetrical anhydrides or carboxylic esters; in the case of ethers—alkyl halides, alkyl mesylates, alkyl triflates, alkyl tosylates or other suitably activated alkyl derivatives; in the case of phosphates and phosphonates—chlorophosphates, dialkyl cyanophosphates, dialkyl dialkylphosphoramidates or chlorophosphites; or in the case of acetals derived from glycosyl groups—using a glycosyl donor e.g. glycosyl halides, thioglycosides, 1-O-acyl glycosides, ortho esters, 1-0 or 1-S carbonates, trichloroimidates, 4-pentenyl glycosides, glycosyl phosphate esters, 1-O-sulfonyls or 1-O-silylated glycosides.

In process (a), 39-desmethoxy-39-methylrapamycin analogues of formula (II) may be prepared as described in WO 2004/007709.

In addition to the specific methods and references provided herein a person of skill in the art may also consult standard textbook references for synthetic methods, including, but not limited to Vogel's textbook of practical organic chemistry (Furniss et al., 1989) and March's advanced organic chemistry (Smith and March, 2001).

Additionally present hydroxyl groups can be protected by one of many standard hydroxy protection strategies available to one skilled in the art. Hydroxyl groups may be protected by forming ethers, including, but not limited to, substituted alkyl ethers, substituted benzyl ethers and silyl ethers. Preferably a silyl ether, including, but not limited to, trimethylsilyl, triethylsilyl, t-butyldimethylsilyl and t-butyldiphenylsilyl, ether is formed by reacting an activated form of the silane (including, but not limited to, silyl chloride or silyl triflate) with 39-desmethoxy-39-methylrapamycin in the presence of a suitable base. The protecting group could then be removed by either acid hydrolysis or fluoride assisted cleavage. 1,2-Diols may be protected as acetonides, based on the condensation of an acetone derivative. This may be removed by acid catalysis.

The 39-desmethoxy-39-methylrapamycin analogues of formula (II) may be used as templates for further semi-synthesis (i.e. process (a)). The pendant hydroxyl group at C-40 can be functionalised by e.g. acylation, alkylation, glycosylation or phosphorylation via a number of synthetic transformations known to a person skilled in the art.

In process (a), when $R_6$ represents a moiety of formula —C(O)$R_7$ or Y—$R_{15}$ where $R_{15}$ represents

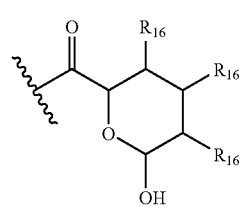

and Y=bond, the formation of a hydroxy ester, or O-acylation, can be mediated by reaction of the hydroxyl group of the compounds of formula (II) with a corresponding carboxylic acid preferably in activated form, for example a compound of formula (IIIAi) or (IIIAii):

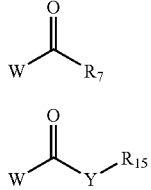
(IIIAi)

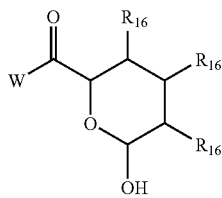
(IIIAii)

or with a compound of formula (IIIB):

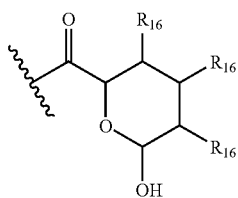
(IIIB)

where W is a group which activates a carboxylic acid to nucleophilic attack. Carboxylic acids can be activated by the formation of for example but without limitation, acyl halides (e.g. W=Cl), mixed anhydrides (i.e. W=OC(O)R'), symmetrical anhydrides (W=OC(O)$R_7$) or carboxylic esters (i.e. W=OR').

Compounds of formula (IIIAi), (IIIAii) or (IIIB) can be prepared from their commercially available carboxylic acids using standard methods known to a person of skill in the art, and in a specific aspect compounds according to formula (IIIAi) wherein $R_7$ is —$(CR_8R_9)_m(CR_{10}R_{11})_pCR_{12}R_{13}R_{14}$ may be prepared using methods as described in U.S. Pat. Nos. 5,362,718, 5,665,772 or EP 0 663 916.

Preferably a 39-desmethoxy-39-methylrapamycin analogue is reacted in organic media with either an acid chloride or mixed anhydride in the presence of a base. Bases which may be used include, but are not limited to, pyridine, 4,4-dimethylaminopyridine (DMAP), 2,6-lutidine, 2,6-di-tert-butylpyridine, triethylamine, diisopropylethylamine, other trialkylamines, 1,8-diazabicyclo[5.4.0]undec-7-ene (DBU) or 1,5-diazabicyclo[4.3.0]non-5-ene (DBN).

In process (a), when $R_6$ represents a moiety of formula —C(O)$R_7$ or Y—$R_{15}$ where $R_{15}$ represents

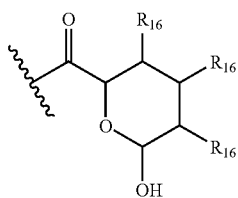

and Y=—C(O)O— or —(CH$_2$)$_2$—OC(O)O— the formation of these hydroxy esters, requires the reaction of the hydroxyl group of the compounds of formula (II) with a reagent that will form an activated carbonate such as a compound of formula IV

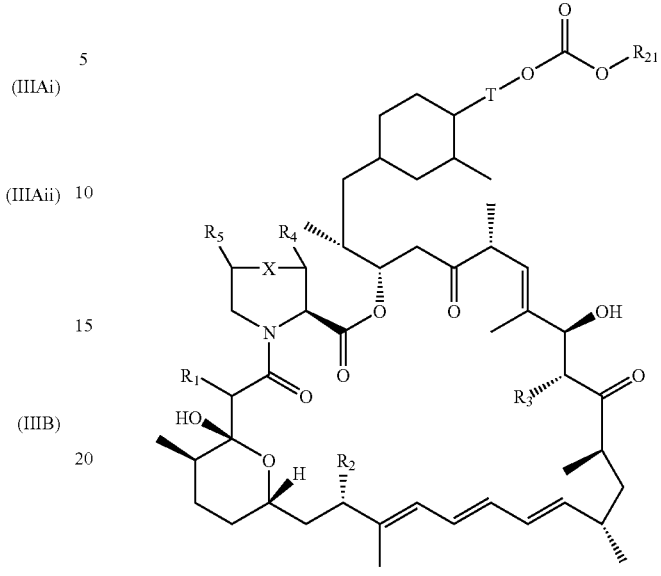

(IV), where T=bond or —O(CH$_2$)$_2$— and $R_{21}$ is an alkyl or aryl group, preferably an aryl group, especially para-nitrophenyl group.

The compound of formula IV can then react with a compound of formula III, to generate compounds with $R_6$ attached to the 40-hydroxyl group via a carbonate linker (WO 2004/101583).

Likewise a 39-desmethoxy-39-methylrapamycin analogue may be derivatized with different hydroxy ethers at C-40, by reacting the 39-desmethoxy-39-methylrapamycin analogue with a suitably activated alkyl derivative of choice, to form a 39-desmethoxy-39-methyl-40-O-alkylrapamycin derivative. Activated alkyl groups refers to an alkyl group that has been activated by one of many methods, including, but not limited to, formation of alkyl halides (RCl, RI, RBr), alkyl mesylates (ROS(O)$_2$CH$_3$), alkyl triflates (ROS(O)$_2$CF$_3$), alkyl tosylates (ROS(O)$_2$PhMe). The activated alkyl group would then be reacted with a 39-desmethoxy-39-methylrapamycin analogue in organic media in the presence of a suitable base. Standard methods to optimise the reaction conditions may be employed by a person of skill in the art to avoid alkylation at other reactive positions.

Likewise a 39-desmethoxy-39-methylrapamycin analogue may be phosphorylated, and after deprotection of the phosphate esters it can yield a 40-O-phospho-39-desmethoxy-39-methylrapamycin derivative or a 40-O-dialkylphospho-39-desmethoxy-39-methylrapamycin derivative, and salts of these derivatives made by methods known to one skilled in the art. Phosphate esters can be formed directly, or indirectly via an O-phosphite (i.e. (R'O)$_2$POR) in which the trivalent phosphite is oxidised (preferably by the action of a peracid, such as but not limited not mCPBA) to the pentavalent phosphate. Direct phosphorylation methods include, but are not limited to, reaction of a 39-demethoxy-39-methylrapamycin analogue with a protected chlorophosphate (e.g. (BnO)$_2$P(O)Cl, (AlkylO)$_2$P(O)Cl), preferably in the presence of DMAP in organic media, or reaction of a 39-desmethoxy-39-methylrapamycin analogue with phosphorus oxychloride (POCl$_3$), in the presence of a base such as triethylamine, followed by acid hydrolysis of the resultant O-dichlorophosphate (i.e. ROP(O)Cl$_2$), or coupling to a dialkyl cyanophosphate (WO 01/81355). Dialkyl or diaryl chlorophosphate may be generated in situ by the reaction of a dialkyl or diaryl phosphite (i.e. (RO)$_2$P(O)H) with carbon tetrachloride in the presence of base. Methods of forming the O-phosphite (for oxidation to the O-phosphate) include, but are not limited to, coupling a 39-desmethoxy-39-methylrapamcyin analogue with a dialkyl dialkylphosphoramidate (preferably dialkyl diisopropylphosphorylamidate), in the presence of base (preferably tetrazole), or coupling using a chlorophosphite in the presence of base (Evans et al., 1992). The choice of protecting group is important, ethyl and methyl esters of phosphates are not readily hydrolysable under acidic or basic conditions. Preferably the protecting groups include, but are not limited to, benzyl esters (cleaved via sodium iodide/chlorotrimethylsilane promoted hydrolysis, (WO 01/81355)) or 2-cyanoethyl esters (cleaved via mild base catalysed cleavage). Similarly 40-O-dialkylphosphono-39-desmethoxy-39-methylrapamycin derivatives can be generated by reacting a 39-desmethoxy-39-methylrapamycin analogue with a suitable activated (as described above) dialkylphosphonate or dialkylphosphite.

In process (a), when $R_{15}$ represents a moiety of formula

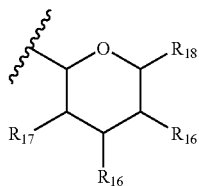

or

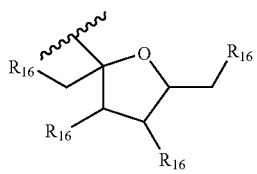

the formation of a glycosidic linkage, or O-glycosylation, can be mediated by reaction of the hydroxyl group with a corresponding glycosyl donor, preferably in activated form, (see Toshima and Tatsuta (1993)) for example a compound of formula (IIIC):

(IIIC)

or a compound of formula (IIID):

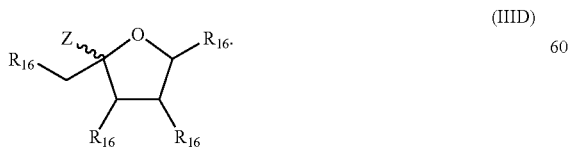

(IIID)

Using a 'glycosyl donor', including, but not limited to, glycosyl halides (Z=F, Cl, Br), thioglycosides (Z=SMe, Set, SPh, SPy, SCN), 1-O-acyl glycosides (Z=OC(O)R), ortho esters (Z=OC(Me)(R)(O—C2 of formula (IIIC/IIID)), 1-O or 1-S carbonates (Z=OC(S)SMe, Z=OC(O)imidazole, Z=OC(S)imidazole, Z=SC(S)OEt), trichloroimidates (Z=OC(=NH)CCl$_3$), 4-pentenyl glycosides (Z=OCH$_2$CH$_2$CH$_2$CH=CH$_2$), phosphate esters (e.g. Z=OP(O)(OPh)$_2$), 1-O-sulfonyls (Z=tosyl), or 1-O-silylated glycosides (Z=OTMS or OTBS), the 39-desmethoxy-39-methylrapamycin analogue may be glycosylated in organic media, preferentially in the presence of an activator (such as a Lewis acid or heavy metal salt, see Toshima and Tatsuta, 1993). The specific glycosyl donor used and the reaction conditions will determine whether an alpha or beta glycoside is formed. As before for acylation, any hydroxyl groups present in the parent compound may be protected or masked such that using one equivalent of glycosyl donor will result in 40-O-acylation. The remaining hydroxyls on the glycosyl donor should be protected, as e.g. O-acetates, O-benzoates, 1,2-acetonides, so a further deprotection will be necessary. Furthermore 2-deoxyglycosyl donors such as glycals may be used (a reductive step is also required) to prepare 2'-deoxy-39-desmethoxy-39-methylrapamycin glycosides and 2,6-dideoxyglycosyl donors such as 2,6-anhydro-2-thiosugars may be used to prepare 2',6'-dideoxy-39-desmethoxy-39-methylrapamycin glycosides.

In process (b), salt formation and exchange may be performed by conventional methods known to a person of skill in the art. Interconversions of compounds of formula (I) may be performed by known processes for example hydroxy and keto groups may be interconverted by oxidation/reduction as described elsewhere herein. Compounds of formula (I) in which $R_6$ represents —PO(OH)$_2$ may be prepared by phosphorylating a corresponding compound of formula (I) in which $R_6$ represents OH. Suitable conditions are provided elsewhere herein.

In processes (a) and (c), examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrolysis, or silyl ether, which may be removed by acidic hydrolysis or fluoride ion assisted cleavage.

In addition to process (a), 39-desmethoxy-39-methylrapamycin analogues of formula (I) where $R_6$ represents $R_7$ can be synthesised by Lipase catalysed transesterification. For example, but without limitation, a 39-desmethoxy-39-methylrapamycin analogue of formula (II) can be reacted with a vinyl ester of formula (V) in the presence of lipase PS-C "Amano" II under the reaction conditions described by Gu et al (2005) and as further set out in the examples herein. This methodology is not limited to the use of vinyl esters and the transesterification may be catalysed by other lipases or esterases.

(V)

Other compounds of the invention may be prepared by methods known per se or by methods analogous to those described above.

The novel 39-desmethoxy-39-methylrapamycin derivatives are useful directly, and as templates for further semi-synthesis or bioconversion, to produce compounds useful as immunosuppressants, antifungal agents, anticancer agents, anti-inflammatory agents, neuroregenerative agents or agents for the treatment of transplantation rejection, graft vs. host disease, autoimmune disorders, vascular disease and/or fibrotic diseases. Methods for the semi-synthetic derivatization of rapamycin and analogues thereof are well known in the art and include (but are not limited to) those modifications described in e.g. U.S. Pat. Nos. 5,665,772; 5,362,718, WO 96/41807; U.S. Pat. Nos. 5,728,710, 5,378,836; 5,138,051; 5,665,772, 5,391,730; 5,023,262, 5,563,145, 5,446,048, 5,912,253, 5,221,670; 5,955,457; WO 98/04279, U.S. Pat. Nos. 6,015,815 and 5,432,183.

The above structures of intermediates (e.g. compounds of formula (II) may be subject to tautomerization and where a representative tautomer is illustrated it will be understood that all tautomers for example keto compounds where enol compounds are illustrated and vice versa are intended to be referred to.

In a further aspect, the present invention provides the use of the 39-desmethoxy-39-methylrapamycin derivatives of the invention in medicine. In a further aspect the present invention provides for the use of 39-desmethoxy-39-methylrapamycin derivatives of the invention in the preparation of a medicament for the induction or maintenance of immunosuppression, the stimulation of neuronal regeneration or the treatment of cancer, B-cell malignancies, fungal infections, transplantation rejection, graft vs. host disease, autoimmune disorders, diseases of inflammation vascular disease and fibrotic diseases or agents for use in the regulation of wound healing.

One skilled in the art would be able by routine experimentation to determine the ability of these compounds to inhibit fungal growth (e.g. Baker, H., et al., 1978; NCCLS Reference method for broth dilution antifungal susceptibility testing for yeasts: Approved standard M27-A, 17(9). 1997). Additionally, one skilled in the art would be able by routine experimentation to determine the ability of these compounds to inhibit tumour cell growth, (see Dudkin, L., et al., 2001; Yu et al. 2001). In a further aspect the compounds of this invention are useful for inducing immunosuppression, assays for determining a compound's efficacy in these areas are well known to those of skill in the art, for example but without limitation: Immunosuppressant activity—Warner, L. M., et al., 1992, Kahan et al. (1991) & Kahan & Camardo, 2001); Allografts Fishbein, T. M., et al., 2002, Kirchner et al. 2000; Autoimmune/Inflammatory/Asthma—Carlson, R. P. et al., 1993; Powell, N. et al., 2001; Diabetes 1—Rabinovitch, A. et al., 2002; Psoriasis—Reitamo, S. et al., 2001; Rheumatoid arthritis—Foey, A., et al., 2002; Fibrosis—Zhu, J. et al., 1999, Jain, S., et al., 2001, Gregory et al. 1993.

The ability of the 39-desmethoxy-39-methylrapamycin derivatives of the invention to induce immunosuppression may be demonstrated in standard tests used for this purpose. In a further aspect the 39-desmethoxy-39-methylrapamycin derivatives of this invention are useful in relation to antifibrotic, neuroregenerative and anti-angiogenic mechanisms, one skilled in the art would be able by routine experimentation to determine the ability of these compounds to prevent angiogenesis (e.g. Guba, M., et al., 2002). One of skill in the art would be able by routine experimentation to determine the utility of these compounds to treat vascular hyperproliferative disease, for example in drug-eluting stents (e.g. Morice, M. C., et al., 2002). Additionally, one of skill in the art would be able by routine experimentation to determine the neuroregenerative ability of these compounds (e.g. Myckatyn, T. M., et al., 2002, Steiner et al. 1997).

The present invention also provides a pharmaceutical composition comprising a 39-desmethoxy-39-methylrapamycin derivative of the invention, together with a pharmaceutically acceptable carrier.

A person of skill in the art will be able to determine the pharmacokinetics and bioavailability of a compound of the invention using in vivo and in vitro methods known to a person of skill in the art, including but not limited to those described below and in the examples, alternative assays are well known to a person of skill in the art including but not limited to those described below and in Gallant-Haidner et al, 2000 and Trepanier et al, 1998 and references therein. The bioavailability of a compound is determined by a number of factors, (e.g. water solubility, rate of absorption in the gut, the extent of protein binding and metabolism) each of which may be determined by in vitro tests as described below, it will be appreciated by a person of skill in the art that an improvement in one or more of these factors will lead to an improvement in the bioavailability of a compound. Alternatively, the bioavailability of a compound may be measured using in vivo methods as described in more detail below.

Caco-2 Permeation Assay

Confluent Caco-2 cells (Li, A. P., 1992; Grass, G. M., et al., 1992, Volpe, D. A., et al., 2001) in a 24 well Corning Costar Transwell format may be used, e.g. as provided by In Vitro Technologies Inc. (IVT Inc., Baltimore, Md., USA). The apical chamber contains 0.15 mL Hank's balanced buffer solution (HBBS) pH 7.4, 1% DMSO, 0.1 mM Lucifer Yellow. The basal chamber contains 0.6 mL HBBS pH 7.4, 1% DMSO. Controls and tests are then incubated at 37° C. in a humidified incubator and shaken at 130 rpm for 1 h. Lucifer Yellow permeates via the paracellular (between the tight junctions) route only, a high Apparent Permeability ($P_{app}$) for Lucifer Yellow indicates cellular damage during assay and all such wells were rejected. Propranolol (good passive permeation with no known transporter effects) & acebutalol (poor passive permeation attenuated by active efflux by P-glycoprotein) are used as reference compounds. Compounds may be tested in a uni- and bi-directional format by applying compound to the apical or basal chamber (at 0.01 mM). Compounds in the apical or basal chambers are analysed by HPLC-MS. Results are expressed as Apparent Permeability, $P_{app}$, (nm/s) and as the Flux Ratio (A to B versus B to A).

$$\text{Papp (nm/s)} = \frac{\text{Volume Acceptor}}{\text{Area} \times [\text{donor}]} \times \frac{\Delta[\text{acceptor}]}{\Delta\text{time}}$$

| | |
|---|---|
| Volume Acceptor: | 0.6 mL (A > B) and 0.15 mL (B > A) |
| Area of monolayer: | 0.33 cm² |
| Δtime: | 60 min |

A positive value for the Flux Ratio indicates active efflux from the apical surface of the cells.

Human Liver Microsomal (HLM) Stability Assay

Liver homogenates provide a measure of a compounds inherent vulnerability to Phase I (oxidative) enzymes, including CYP450s (e.g. CYP2C8, CYP2D6, CYP1A, CYP3A4, CYP2E1), esterases, amidases and flavin monooxygenases (FMOs).

The half life (T1/2) of test compounds can be determined, on exposure to Human Liver Microsomes, by monitoring their disappearance over time by LC-MS. Compounds at 0.001 mM are incubated at for 40 min at 37° C., 0.1 M Tris-HCl, pH 7.4 with human microsomal sub-cellular fraction of liver at 0.25 mg/mL protein and saturating levels of NADPH as co-factor. At timed intervals, acetonitrile is added to test samples to precipitate protein and stop metabolism. Samples are centrifuged and analysed for parent compound by HPLC-MS.

In Vivo Bioavailability Assays

In vivo assays may also be used to measure the bioavailability of a compound (see e.g. Crowe et al, 1999). Generally, a compound is administered to a test animal (e.g. mouse or rat) both intraperitoneally (i.p.) or intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

Mice are dosed with 3 mg/kg of the compound of the invention or the parent compound i.v. or 10 mg/kg of a compound of the invention of the parent compound p.o. Blood samples are taken at 5 minute, 15 minute, 1 h, 4 h and 24 h intervals and the concentration of the compound of the invention or parent compound in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body clearance, steady-state volume of distribution and F %. These parameters are then analysed by non-compartmental or compartmental methods to give a calculated percentage bioavailability, for an example of this type of method see Gallant-Haidner et al, 2000 and Trepanier et al, 1998 and references therein, and references therein.

The aforementioned 39-desmethoxy-39-methylrapamycin derivatives of the invention or a formulation thereof may be administered by any conventional method for example but without limitation they may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The 39-desmethoxy-39-methylraparnycin derivatives of the invention may be administered alone or in combination with other therapeutic agents, co-administration of two (or more) agents allows for significantly lower doses of each to be used, thereby reducing the side effects seen.

In one embodiment, a 39-desmethoxy-39-methylrapamycin derivative is co-administered with another therapeutic agent for the induction or maintenance of immunosuppression, for the treatment of transplantation rejection, graft vs. host disease, autoimmune disorders or diseases of inflammation preferred agents include, but are not limited to, immunoregulatory agents e.g. azathioprine, corticosteroids, cyclophosphamide, cyclosporin A, FK506, Mycophenolate Mofetil, OKT-3 and ATG.

In an alternative embodiment, a 39-desmethoxy-39-methylrapamycin derivative is co-administered with another therapeutic agent for the treatment of cancer or B-cell malignancies preferred agents include, but are not limited to, methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® or hsp90 inhibitors (e.g. 17-AAG or 17-DMAG). Additionally, a 39-desmethoxy-39-methylrapamycin derivative may be administered in combination with other therapies including, but not limited to, radiotherapy or surgery.

In one embodiment, a 39-desmethoxy-39-methylrapamycin derivative is co-administered with another therapeutic agent for the treatment of vascular disease, preferred agents include, but are not limited to, ACE inhibitors, angiotensin II receptor antagonists, fibric acid derivatives, HMG-CoA reductase inhibitors, beta adrenergic blocking agents, calcium channel blockers, antioxidants, anticoagulants and platelet inhibitors (e.g. Plavix™).

In one embodiment, a 39-desmethoxy-39-methylrapamycin derivative is co-administered with another therapeutic agent for the stimulation of neuronal regeneration, preferred agents include, but are not limited to, neurotrophic factors e.g. nerve growth factor, glial derived growth factor, brain derived growth factor, ciliary neurotrophic factor and neurotrophin-3.

In one embodiment, a 39-desmethoxy-39-methylrapamycin derivative is co-administered with another therapeutic agent for the treatment of fungal infections; preferred agents include, but are not limited to, amphotericin B, flucytosine, echinocandins (e.g. caspofungin, anidulafungin or micafungin), griseofulvin, an imidazole or a triazole antifungal agent (e.g. clotrimazole, miconazole, ketoconazole, econazole, butoconazole, oxiconazole, terconazole, itraconazole, fluconazole or voriconazole).

By co-administration is included any means of delivering two or more therapeutic agents to the patient as part of the same treatment regime, as will be apparent to the skilled person. Whilst the two or more agents may be administered simultaneously in a single formulation this is not essential. The agents may administered in different formulations and at different times.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The 39-desmethoxy-39-methylrapamycin derivatives of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of 39-desmethoxy-39-methylrapamycin derivatives suitable for oral administration may also contain excipients e.g. N,N-dimethylacetamide, dispersants e.g. polysorbate 80, surfactants, and solubilizers, e.g. polyethylene glycol, Phosal 50 PG (which consists of phosphatidylcholine, soya-fatty acids, ethanol, mono/diglycerides, propylene glycol and ascorbyl palmitate), Such tablets may contain excipients such as microcrystalline cellulose, lactose (e.g. lactose monohydrate or lactose anhydrous), sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compounds of the invention may also be administered using medical devices known in the art. For example, in one embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment the 39-desmethoxy-39-methylrapamycin derivative may be administered using a drug-eluting stent, for example corresponding to those described in WO 01/87263 and related publications or those described by Perin (Perin, 2005). Many other such implants, delivery systems, and modules are known to those skilled in the art.

The dosage to be administered of a 39-desmethoxy-39-methylrapamycin derivative of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

EXAMPLES

General Methods and Materials

Materials

Figure 1:
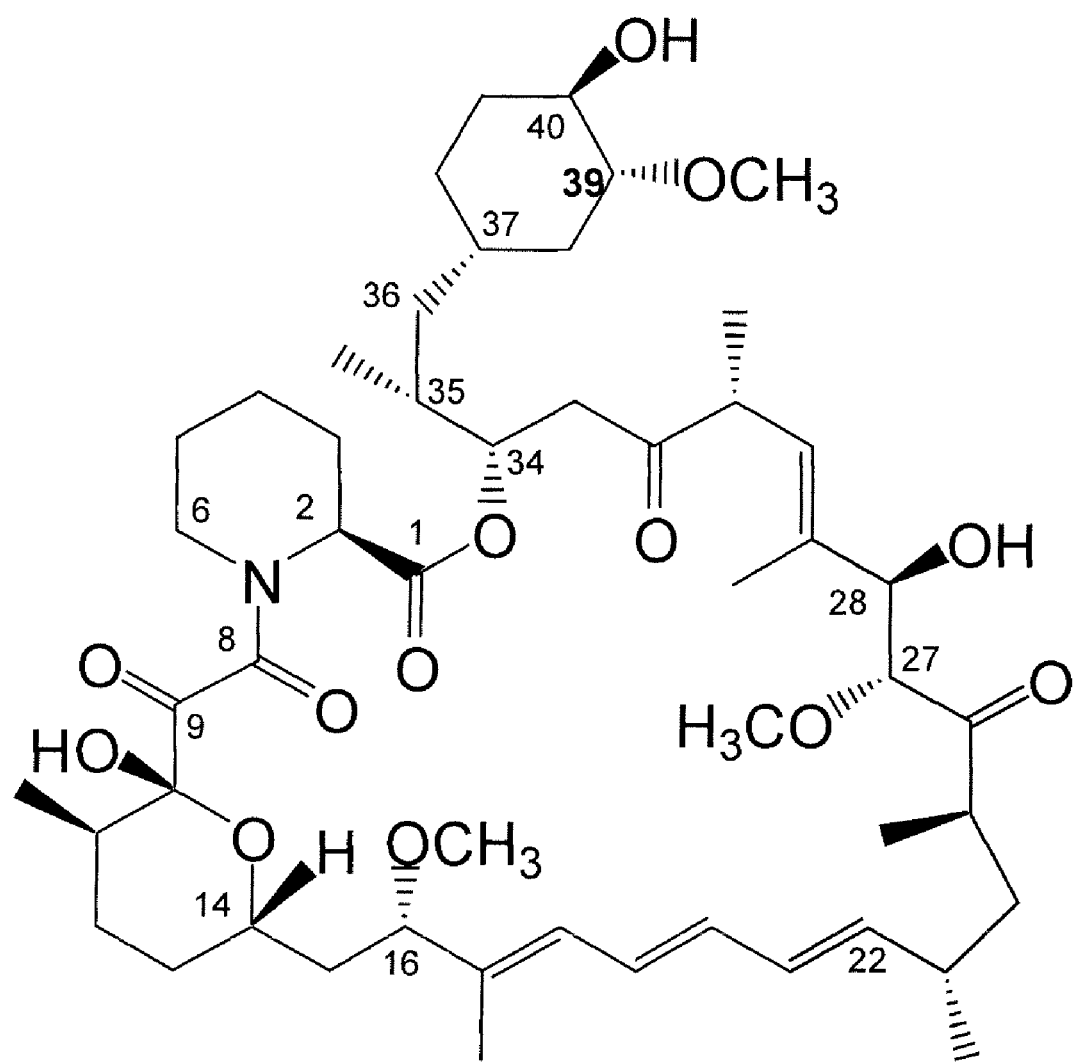
FIG. 1: shows the structure of rapamycin

All reagents were obtained from commercial sources, and used without further purification unless stated otherwise.

Culture

*S. hygroscopicus* MG2-10 [JMNOQLhis] was maintained on medium 1 agar plates (see below) at 28° C. Spore stocks were prepared after growth on medium 1, preserved in 20% w/v glycerol:10% w/v lactose in distilled water and stored at −80° C. Vegetative cultures were prepared by inoculating 0.1 mL of frozen stock into 50 mL medium 2 (see below) in 250 mL flask. The culture was incubated for 36 to 48 hours at 28° C., 300 rpm.

Production Method:

Vegetative cultures were inoculated at 2.5-5% v/v into medium 3. Cultivation was carried out for 6-7 days, 26° C., 300 rpm.

Feeding Procedure:

The feeding/addition of the selected carboxylic acid was carried out 24-48 hours after inoculation and was fed at 1-2 mM unless stated otherwise.

Medium 1:

| component | Source | Catalogue # | Per L |
|---|---|---|---|
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | Difco | 2140-10 | 20 g |
| Wheat starch | Sigma | S2760 | 10 g |
| Water to | | | 1 L |

The media was then sterilised by autoclaving 121° C., 20 min.

Medium 2: Rap V7 Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| Glucose | 10 g |
| $(NH_4)_2SO_4$ | 2 g |
| Lactic acid (80%) | 1.6 mL |
| $CaCO_3$ (Caltec) | 7 g |

Adjust pH to 7.5 with 1 M NaOH.

The media was then sterilised by autoclaving 121° C., 20 min.

After sterilisation 0.16 mL of 40% glucose is added to each 7 mL of media.

Medium 3: MD6 Medium (Fermentation Medium)

| Component | Per L |
|---|---|
| Toasted Nutrisoy (ADM Ingredients Ltd) | 30 g |
| Corn starch (Sigma) | 30 g |
| Avedex W80 dextrin (Deymer Ingredients Ltd) | 19 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 5 g |
| $CaCO_3$ (Caltec) | 10 g |
| $MnCl_2 \cdot 4H_2O$ | 10 mg |
| $MgSO_4 \cdot 7H_2O$ | 2.5 mg |
| $FeSO_4 \cdot 7H_2O$ | 120 mg |
| $ZnSO_4 \cdot 7H_2O$ | 50 mg |
| MES (2-morpholinoethane sulphuric acid monohydrate) | 21.2 g | pH is corrected to 6.0 with 1 M NaOH

Before sterilization 0.4 mL of Sigma α-amylase (BAN 250) was added to 1 L of medium.

Medium was sterilised for 20 min at 121° C.

After sterilisation 0.35 mL of sterile 40% fructose and 0.10 mL of L-lysine (140 mg/mL in water, filter-sterilized) was added to each 7 mL.

Medium 4: Rap V7a Seed Medium

| Component | Per L |
|---|---|
| Toasted Nutrisoy (ADM Ingredients Ltd) | 5 g |
| Avedex W80 dextrin (Deymer Ingredients Ltd) | 35 g |

-continued

| Component | Per L |
|---|---|
| Corn Steep Solids (Sigma) | 4 g |
| $(NH_4)_2SO_4$ | 2 g |
| Lactic acid (80%) | 1.6 mL |
| $CaCO_3$ (Caltec) | 7 g |

Adjust pH to 7.5 with 1 M NaOH.

The media was then sterilised by autoclaving 121° C., 20 min

Medium 5: MD6/5-1 medium (Fermentation Medium)

| Component | Per L |
|---|---|
| Toasted Nutrisoy (ADM Ingredients Ltd) | 15 g |
| Avedex W80 dextrin (Deymer Ingredients Ltd) | 50 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 13 g |
| $CaCO_3$ (Caltec) | 10 g |
| $MnCl_2\ 4H_2O$ | 3.5 mg |
| $MgSO_4\ 7H_2O$ | 15 mg |
| $FeSO_4\ 7H_2O$ | 150 mg |
| $ZnSO_4\ 7H_2O$ | 60 mg |
| SAG 471 | 0.1 ml |

Medium was sterilised for 30 min at 121° C.

After sterilisation 15 g of Fructose per L was added.

After 48 h 0.5 g/L of L-lysine was added.

Synthetic Methods

All reactions were carried out under anhydrous conditions unless stated otherwise using commercially available dried solvents. Reactions were monitored by LC-UV-MS, on an Agilent 1100 HPLC coupled to a Bruker Daltonics Esquire3000+ mass spectrometer equipped with an electrospray source. Separation was achieved over a Phenomenex Hyperclone column, BDS $C_{18}$ 3u (150×4.6 mm) at 1 mL/min, with a linear gradient of water:acetonitrile v:v 30:70 to 100% acetonitrile over 10 min followed by an isocratic period of 5 min at 100% acetonitrile.

In Vitro Bioassay for Anticancer Activity

In vitro evaluation of compounds for anticancer activity in a panel of 12 human tumour cell lines in a monolayer proliferation assay may be carried out at the Oncotest Testing Facility, Institute for Experimental Oncology, Oncotest GmbH, Freiburg. The characteristics of the 12 selected cell lines is summarised in Table 1.

TABLE 1

Test cell lines

| # | Cell line | Characteristics |
|---|---|---|
| 1 | MCF-7 | Breast, NCI standard |
| 2 | MDA-MB-231 | Breast - PTEN positive, resistant to 17-AAG |
| 3 | MDA-MB-468 | Breast - PTEN negative, resistant to 17-AAG |
| 4 | NCI-H460 | Lung, NCI standard |
| 5 | SF-268 | CNS, NCI standard |
| 6 | OVCAR-3 | Ovarian - p85 mutated. AKT amplified. |
| 7 | A498 | Renal, high MDR expression, |
| 8 | GXF 251L | Gastric |

TABLE 1-continued

Test cell lines

| # | Cell line | Characteristics |
|---|---|---|
| 9 | MEXF 394NL | Melanoma |
| 10 | UXF 1138L | Uterus |
| 11 | LNCAP | Prostate - PTEN negative |
| 12 | DU145 | Prostate - PTEN positive |

The Oncotest cell lines are established from human tumor xenografts as described by Roth et al. 1999. The origin of the donor xenografts was described by Fiebig et al. 1999. Other cell lines are either obtained from the NCI (H460, SF-268, OVCAR-3, DU145, MDA-MB-231, MDA-MB-468) or purchased from DSMZ, Braunschweig, Germany (LNCAP).

All cell lines, unless otherwise specified, are grown at 37° C. in a humidified atmosphere (95% air, 5% $CO_2$) in a 'ready-mix' medium containing RPMI 1640 medium, 10% fetal calf serum, and 0.1 mg/mL gentamicin (PAA, Cölbe, Germany).

Monolayer Assay—Brief Description of Protocol:

A modified propidium iodide assay may be used to assess the effects of the test compound(s) on the growth of twelve human tumour cell lines (Dengler et al., (1995)).

Briefly, cells are harvested from exponential phase cultures by trypsinization, counted and plated in 96 well flat-bottomed microtitre plates at a cell density dependent on the cell line (5-10,000 viable cells/well). After 24 h recovery to allow the cells to resume exponential growth, 0.01 mL of culture medium (6 control wells per plate) or culture medium containing the test compound are added to the wells. Each concentration is plated in triplicate. Compounds are applied in two concentrations (0.001 µM and 0.01 µM). Following 4 days of continuous exposure, cell culture medium with or without test compound is replaced by 0.2 mL of an aqueous propidium iodide (PI) solution (7 mg/L). To measure the proportion of living cells, cells are permeabilized by freezing the plates. After thawing the plates, fluorescence is measured using the Cytofluor 4000 microplate reader (excitation 530 nm, emission 620 nm), giving a direct relationship to the total number of viable cells.

Growth inhibition is expressed as treated/control×100 (% T/C). For active compounds, $IC_{50}$ & $IC_{70}$ values may be estimated by plotting compound concentration versus cell viability.

Example 1

Fermentation and Isolation of 39-desmethoxy-39-methylrapamycin 39-desmethoxy-39-methylrapamycin was produced according to the methods described in WO 04/007709. Briefly, cultures of S. hygroscopicus MG2-10 were transformed with an appropriate expression vector carrying the rapamycin genes rapJ, rapM rapN, rapO, rapQ and rapL to produce strain S. hygroscopicus MG2-10[rapJMNOQLhis]. Cultures of S. hygroscopicus MG2-10[rapJMNOQLhis] were grown and fed with 3-methylcyclohexanecarboxylic acid using the methods described in WO 04/007709. LCMS and LCMS" analysis of culture extracts showed that the m/z ratio for the rapamycin analogue produced was 16 atomic mass units lower than that for rapamycin, and was consistent with the exchange of a methoxy group for a methyl group at C-39.

Example 2

Synthesis of 39-desmethoxy-39-methyl-40-O-[2,2-bis(hydroxymethyl)propionyl]rapamycin Through Lipase Catalysed Esterification of 39-desmethoxy-39-methylrapamycin A mixture of 39-desmethoxy-39-methylrapamycin, vinyl 2,2,5-trimethyl[1.3-dioxane]-5-carboxylate, lipase PS-C "Amano" II and molecular sieves (0.5 nm) in anhydrous tert-Butyl methyl ether is heated to 43° C. under an atmosphere of argon. After 48 h LC/MS monitoring shows conversion of the starting material. THF is added and the mixture is filtered through a pad of celite. The enzyme is washed twice with THF and the combined organic extracts are concentrated under reduced pressure. The residue is dissolved in THF and $H_2SO_4$ (0.5 N) is added. The solution is allowed to stand at room temperature for 5 h after which the reaction is subsequently quenched by the addition of $NaHCO_3$ (5%) and brine. The aqueous mixture is extracted three times with ethyl acetate and the combined organic extracts are dried over $MgSO_4$. Removal of solvents gives the product as a semi-solid. Purification by flash chromatography (hexane/acetone 1:1) gives the product as a colourless solid.

Example 3

39-desmethoxy-39-methyl-40-O-(2-hydroxy)ethyl Rapamycin

3.1. 2-(tert-butyldimethylsilyl)oxyethyl Triflate

A solution of 2-(tert-butyldimethylsilyl)-ethylene glycol (125 mg, 0.71 mmol) and 2,6-lutidene (0.08 mL, 0.69 mmol) in 6 mL dichloromethane was cooled to −78° C. Trifluoromethanesulfonic anhydride (0.11 mL, 0.65 mmol) was added over a period of 5 min and stirring was continued for additional 15 min at −78° C. to complete the formation of the triflate. The triflate was used in situ for the reaction as described in 3.2 below.

3.2. 40-O-[2-(tert-butyldimethylsilyl)]ethyl-39-desmethoxy-39-Methylrapamycin 39-Desmethoxy-39-methylrapamycin and 2,6-di-tert-butylpyridine are treated with 2-(tert-butyldimethylsilyl)oxyethyl triflate at room temperature. This solution is then concentrated to a third of its original volume with a gentle stream of nitrogen and the resulting suspension is stirred for further 72 h at room temperature. After that period saturated sodium hydrogen carbonate solution and water are added and the mixture is stirred for approximately 30 min. The organic layer is separated and the aqueous phase is extracted twice with ethyl acetate. The combined organic extracts are dried over sodium sulfate and concentrated under reduced pressure to give a colourless oil. Purification by column chromatography on silica using a gradient from hexane to hexane/acetone (v:v 1:1) gives the product as a colourless solid.

3.3. 39-Desmethoxy-39-methyl-40-O-(2-hydroxy)ethyl Rapamycin

A solution of 40-O-[2-(tert-butyldimethylsilyl)]ethyl-39-desmethoxy-39-methylrapamycin in acetone is treated with 0.5 N sulfuric acid at room temperature. The solution is allowed to stand at room temperature for approximately 3 h and is subsequently quenched by the addition of saturated sodium hydrogen carbonate solution and water. The aqueous mixture is then extracted three times with ethyl acetate and the combined organic extracts are dried over sodium sulfate. Concentration under reduced pressure gives a colourless solid which may be further purified by HPLC (water/acetonitrile v:v 20/80).

Example 4

Synthesis of 39-desmethoxy-39-methyl-40-O-[2,2-bis(hydroxymethyl)propionyl]Rapamycin 39-Desmethoxy-39-methyl-40-O-[2,2-bis(hydroxymethyl)propionyl]rapamycin is synthesised from 39-desmethoxy-39-methylrapamycin according to the following procedure.

4.1 Synthesis of 39-desmethoxy-39-methyl-28-O-trimethylsilyl Rapamycin

39-Desmethoxy-39-methylrapamycin and imidazole are dissolved in ethyl acetate at 0° C. To this cold solution chlorotrimethylsilane is added drop wise over a period of 10 min. Stirring is continued for an additional 60 min to complete the formation of the 28,39-bis-O-trimethylsilyl ether. After that period aqueous sulfuric acid (0.5 N) is added and the mixture is stirred for 2.5 h at 0° C. Ethyl acetate is then added and the organic layer is washed with brine, saturated sodium hydrogen carbonate solution and water. Drying over sodium sulfate and concentration under reduced pressure yields the 28-O-trimethylsilyl ether as a colourless solid which is used without further purification for the subsequent reaction.

4.2. Synthesis of 2,4,6-trichlorobenzoic 2',2',5'-trimethyl-1,3'-dioxane-5' Carboxylic Anhydride 2,2-Dimethoxypropane (13.5 g, 130 mmol) and p-toluenesulfonic acid monohydrate (100 mg, 0.53 mmol, 0.4 mol %) were added to a solution of 2,2-bis(hydroxymethyl)propionic acid (13.5 g, 100 mmol) in acetone (100 mL). The reaction mixture was stirred at room temperature for 2 h. After that period moist sodium hydrogen carbonate was added and the mixture was stirred for further 5 minutes. The supernatant was decanted off and concentrated under reduced pressure. The resulting solid was treated with diethyl ether (3×50 mL) and the combined organic extracts were concentrated under reduced pressure to yield a white solid, 16.2 g (93%)

$^1$H-NMR (400 MHz, $CDCl_3$), δ (ppm): 4.19 (d, 1H, J=12.0 Hz) 3.68 (d, 1H, J=12.0 Hz) 1.45 (s, 1H) 1.41 (s, 1H) 1.20 (s, 1H).

This material was then converted into an activated mixed anhydride by the method of U.S. Pat. No. 5,362,718. Thus, the acetonide (1.04 g, 5.98 mmol) was dissolved in THF (20 mL) cooled to 0° C. and treated with the dropwise addition of triethylamine (0.83 mL, 5.98 mmol) and 2,4,6-trichlorobenzoyl chloride (0.93 mL, 5.98 mmol). The reaction was then stirred at room temperature for 5 hours. The resulting precipitate was filtered and washed with THF (10 mL). The combined filtrate was reduced in vacuo to a white amorphous solid which was used (as below) without further purification.

4.3. Synthesis of 39-desmethoxy-39-methylrapamycin 28-O-trimethylsilyl Ether, 40-ester with 2,2,5-trimethyl[1.3-dioxane]-5-carboxylic Acid Crude 28-O-trimethylsilyl-39-desmethoxy-39-methylrapamycin from example 4.1 is dissolved in dichloromethane. The solution is cooled to 0° C. and DMAP is added. Then, a solution of 2,4,6-trichlorobenzoic 2',2',5'-trimethyl-1',3'-dioxane-5' carboxylic anhydride in dichloromethane is added over a period of 10 min. The reaction mixture is stirred at 0° C. for 5 h and the conversion is monitored by LC/MS. The reaction mixture is diluted with dichloromethane and quenched by addition of water. The organic layer is separated and washed successively with sulfuric acid (0.5 N), sodium hydrogen carbonate solution and water. Drying over sodium sulfate and concentration under reduced pressure give the title compound as colourless foam, which is used immediately without further purification.

4.4. 39-desmethoxy-39-methyl-40-O-[2,2-bis(hydroxymethyl)propionyl]rapamycin Crude 39-desmethoxy-39-methylrapamycin-28-O-trimethylsilyl ether 40-ester with 2,2,5-trimethyl[1.3-dioxane]-5-carboxylic acid from example 4.3 is dissolved in acetone and sulfuric acid (0.5 N) is added. The reaction mixture is stirred for 5 h at room temperature and subsequently neutralised by the addition of saturated sodium hydrogen carbonate solution and water. The aqueous mixture is extracted with ethyl acetate and the combined organic extracts are dried over sodium sulphate. Concentration under reduced pressure gives a colourless solid which is purified by size exclusion chromatography on Sephadex LH20 using chloroform/heptane/ethanol (v:v:v 10:10:1) as eluents.

REFERENCES

Alarcon, C. M., Heitman, J., and Cardenas, M. E. (1999) Protein kinase activity and identification of a toxic effector domain of the target of rapamycin TOR proteins in yeast. *Molecular Biology of the Cell* 10: 2531-2546.

Aparicio, J. F., Molnár, I., Schwecke, T., König, A., Haydock, S. F., Khaw, L. E., Staunton, J., and Leadlay, P. F. (1996) Organization of the biosynthetic gene cluster for rapamycin in *Streptomyces hygroscopicus*: analysis of the enzymatic domains in the modular polyketide synthase. *Gene* 169: 9-16.

Baker, H., Sidorowicz, A., Sehgal, S. N., and Vézina, C. (1978) Rapamycin (AY-22,989), a new antifungal antibiotic. III. In vitro and in vivo evaluation. *Journal of Antibiotics* 31: 539-545.

Boulay, A., Zumstein-Mecker, S., Stephan, C., Beuvink, I., Zilbermann, F., Haller, R., Tobler, S., Heusser, C., O'Reilly, T., Stolz, B., Marti, A., Thomas, G., Lane, H. A., 2004, Antitumor efficacy of intermittent treatment schedules with the rapamycin derivative RAD001 correlates with prolonged inactivation of ribosomal protein S6 kinase 1 in peripheral blood mononuclear cells. *Cancer Res.* 64(1), 252-61.

Brown, E. J., Albers, M. W., Shin, T. B., Ichikawa, K., Keith, C. T., Lane, W. S., and Schreiber, S. L. (1994) A mammalian protein targeted by G1-arresting rapamycin-receptor complex. *Nature* 369: 756-758.

Brunn, G. J., Williams, J., Sabers, C., Wiederrecht, G., Lawrence, J. C., and Abraham, R. T. (1996) Direct inhibition of the signaling functions of the mammalian target of rapamycin by the phosphoinositide 3-kinase inhibitors, wortmannin and LY294002. *EMBO Journal* 15: 5256-5267.

Carlson, R. P., Hartman, D. A., Tomchek, L. A., Walter, T. L., Lugay, J. R., Calhoun, W., Sehgal, S. N., Chang, J. Y. (1993). Rapamycin, a potential disease-modifying antiarthritic drug. J. Pharmacol. Exp. Ther. 266(2): 1125-38.

Crowe A, Bruelisauer A, Duerr L, Guntz P, Lemaire M. (1999) Absorption and intestinal metabolism of SDZ-RAD and rapamycin in rats. *Drug Metab Dispos*, 27(5), 627-32

Dengler W. A., Schulte J., Berger D. P., Mertelsmann R. and Fiebig H H. (1995) Development of a propidium iodide fluorescence assay for proliferation and cytotoxicity assay. *Anti-Cancer Drugs*, 6:522-532.

DiLella, A. G., and Craig, R. J. (1991) Exon organization of the human FKBP-12 gene: correlation with structural and functional protein domains. *Biochemistry* 30: 8512-8517.

Dudkin, L., Dilling, M. B., Cheshire, P. J., Harwood, F. C., Hollingshead, M., Arbuck, S. G., Travis, R., Sausville, E. A., Houghton, P. J. (2001). Biochemical correlates of mTOR inhibition by the rapamycin ester CCI-779 and tumor growth inhibition. Clin. Cancer Res. 7(6):1758-64

Evans D. A., Gage J. R. and Leighton J. L. (1992) Assymetric synthesis of calyculin A. 3. Assemblage of the calyculin skeleton and the introduction of a new phosphate monoester synthesis. *J. Org. Chem.*, 57:1964-1966

Fiebig H. H., Dengler W. A. and Roth T. (1999) Human tumor xenografts: Predictivity, characterization, and discovery of new anticancer agents. In:

Fiebig H H, Burger A M (eds). Relevance of Tumor Models for Anticancer Drug Development. *Contrib. Oncol.*, 54: 29-50.

Findlay J. A, and Radics, L. (1980) *Canadian Journal of Chemistry* 58:579.

Fishbein, T. M., Florman, S., Gondolesi, G., Schiano, T., LeLeiko, N., Tschernia, A., Kaufman, S. (2002). Intestinal transplantation before and after the introduction of sirolimus. *Transplantation*. 73(10): 1538-42.

Foey, A., Green, P., Foxwell, B., Feldmann, M., Brennan, F. (2002). Cytokine-stimulated T cells induce macrophage IL-10 production dependent on phosphatidylinositol 3-kinase and p70S6K: implications for rheumatoid arthritis. *Arthritis Res.* 4(1):64-70. Epub 2001 Oct. 10.

Furniss B. S., Hannaford A. J., Smith P. W. G. and Tatchell A. R. (1989) *Vogel's textbook of practical organic chemistry*, 5th Ed, Pearson, Prentice Hall, Harlow, UK.

Gallant-Haidner H L, Trepanier D J, Freitag D G, Yatscoff R W. 2000, "Pharmacokinetics and metabolism of sirolimus". *Ther Drug Monit.* 22(1), 31-5.

Grass, G. M., Rubas, W., Jezyk, N., (1992) Evaluation of CACO-2 monolayers as a predictor of drug permeability in colonic tissues. *FASEB Journal*, 6, A1002.

Gregory, C. R., Huie, P., Billingham, M. E. and Morris, R. E. (1993). Rapamycin inhibits arterial intimal thickening caused by both alloimmune and mechanical injury. Its effect on cellular, growth factor and cytokine response in injured vessels. *Transplantation* 55(6): 1409-1418.

Gregory M A, Gaisser S, Lill R E, Hong H, Sheridan R M, Wilkinson B, Petkovic H, Weston A J, Carletti I, Lee H L, Staunton J, Leadlay P F. (2004) "Isolation and characterization of pre-rapamycin, the first macrocyclic intermediate in the biosynthesis of the immunosuppressant rapamycin by *S. hygroscopicus*". *Angew Chem Int Ed Engl.* 43(19), 2551-3

Gu, J, Ruppen M E, Cai P. (2005), "Lipase-Catalyzed Regioselective Esterification of Rapamycin: Synthesis of Temsirolimus (CCI-779). Org. Lett. 7(18): 3945-3948.

Guba, M., von Breitenbuch, P., Steinbauer, M., Koehl, G., Flegel, S., Hornung, M., Bruns, C. J., Zuelke, C., Farkas, S., Anthuber, M., Jauch, K. W., and Geissler, E. K. (2002)

Rapamycin inhibits primary and metastatic tumor growth by antiangiogenesis: involvement of vascular endothelial growth factor. *Nature Medicine* 8: 128-135.

Hardwick, J. S., Kuruvilla, F. G., Tong, J. K., Shamji, A. F., and Schreiber, S. L. (1999) Rapamycin-modulated transcription defines the subset of nutrient-sensitive signaling pathways directly controlled by the Tor proteins. *Proceedings of the National Academy of Sciences of the United States of America* 96: 14866-14870.

Hentges, K. E., Sirry, B., Gingeras, A. C., Sarbassov, D., Sonenberg, N., Sabatini, D., and Peterson, A. S. (2001) FRAP/mTOR is required for proliferation and patterning during embryonic development in the mouse. *Proceedings of the National Academy of Sciences of the United States of America* 98: 13796-13801.

Jain, S., Bicknell, G. R., Whiting, P. H., Nicholson, M. L. (2001). Rapamycin reduces expression of fibrosis-associated genes in an experimental model of renal ischaemia reperfusion injury. *Transplant Proc.* 33(1-2):556-8.

Kahan, B. D., and Camardo, J. S. (2001) Rapamycin: Clinical results and future opportunities. *Transplantation* 72:1181-1193.

Kahan, B. D., Chang, J. Y., and Sehgal, S. N. (1991) Preclinical evaluation of a new potent immunosuppressive agent, rapamycin. *Transplantation* 52: 185-191.

Kirby, B., and Griffiths, C. E. M. (2001) Psoriasis: the future. *British Journal of Dermatology* 144:37-43.

Kirchner, G. I., Winkler, M., Mueller L., Vidal, C., Jacobsen, W., Franzke, A., Wagner, S., Blick, S., Manns M. P., and Sewing K.-F. (2000) Pharmacokinetics of SDZ RAD and cyclosporin including their metabolites in seven kidney graft patients after the first dose of SDZ RAD. *British Journal of Clinical Pharmacology* 50:449-454.

Kuo, C. J., Chung, J. K., Fiorentino, D. F., Flanagan, W. M., Blenis, J., and Crabtree, G. R. (1992) Rapamycin selectively inhibits interleukin-2 activation of p70 S6 kinase. *Nature* 358: 70-73.

Li, A. P. (1992) Screening for human ADME/Tox drug properties in drug discovery. *Drug Discovery Today*, 6, 357-366.

Lyons, W. E., George, E. B., Dawson, T. M., Steiner, J. P., and Snyder, S. H. (1994) Immunosuppressant FK506 promotes neurite outgrowth in cultures of PC12 cells and sensory ganglia. *Proceedings of the National Academy of Sciences of the United States of America* 91:3191-3195.

McAlpine, J. B, Swanson S. J., Jackson, M., Whittern, D. N. (1991). Revised NMR assignments for rapamycin. *Journal of Antibiotics* 44: 688-690.

Morice, M. C., Serruys, P. W., Sousa, J. E., Fajadet, J., Ban Hayashi, E., Perin, M., Colombo, A., Schuler, G., Barragan, P., Guagliumi, G., Molnar, F., Falotico, R. (2002). RAVEL Study Group. Randomized Study with the Sirolimus-Coated Bx Velocity Balloon-Expandable Stent in the Treatment of Patients with de Novo Native Coronary Artery Lesions. A randomized comparison of a sirolimus-eluting stent with a standard stent for coronary revascularization. *N. Engl.l J. Med* 346(23):1773-80.

Myckatyn, T. M., Ellis, R. A., Grand, A. G., Sen, S. K., Lowe, J. B. 3rd, Hunter, D. A., Mackinnon, S. E. (2002). The effects of rapamycin in murine peripheral nerve isografts and allografts. *Plast Reconstr. Surg.* 109(7):2405-17.

Navé, B. T., Ouwens, D. M., Withers, D. J., Alessi, D. R., and Sheperd, P. R. (1999) Mammalian target of rapamycin is a direct target for protein kinase B: identification of a convergence point for opposing effects of insulin and amino-acid deficiency on protein translation. *Biochemical Journal* 344:427-431.

NCCLS Reference Method for Broth Dilution Antifungal Susceptibility Testing for Yeasts: Approved Standard M27-A, vol. 17 No. 9. (1997).

Paiva, N. L., Demain, A. L., and Roberts, M. F. (1991) Incorporation of acetate, propionate, and methionine into rapamycin By *Streptomyces hygroscopicus*. *Journal of Natural Products* 54: 167-177.

Paiva, N. L., Demain, A. L., and Roberts, M. F. (1993) The immediate precursor of the nitrogen-containing ring of rapamycin is free pipecolic acid. *Enzyme and Microbial Technology* 15: 581-585.

Perin, E C, (2005), "Choosing a Drug-Eluting Stent: A Comparison Between CYPHER and TAXUS", *Reviews in Cardiovascular Medicine*, 6 (suppl 1), pp S13-S21.

Powell, N., Till, S., Bungre, J., Corrigan, C. (2001). The immunomodulatory drugs cyclosporin A, mycophenolate mofetil, and sirolimus (rapamycin) inhibit allergen-induced proliferation and IL-5 production by PBMCs from atopic asthmatic patients. *J. Allergy Clin. Immunol.* 108(6): 915-7

Rabinovitch, A., Suarez-Pinzon, W. L., Shapiro, A. M., Rajotte, R. V., Power, R. (2002). Combination therapy with sirolimus and interleukin-2 prevents spontaneous and recurrent autoimmune diabetes in NOD mice. *Diabetes.* 51(3):638-45.

Raught, B., Gingras, A. C., and Sonenberg, N. (2001) The target of rapamycin (TOR) proteins. *Proceedings of the National Academy of Sciences of the United States of America* 98: 7037-7044.

Reather, J. A., (2000), Ph.D. Dissertation, University of Cambridge. "Late steps in the biosynthesis of macrocyclic lactones".

Reitamo, S., Spuls, P., Sassolas, B., Lahfa, M., Claudy, A., Griffiths, C. E.; Sirolimus European Psoriasis Study Group. (2001). Efficacy of sirolimus (rapamycin) administered concomitantly with a subtherapeutic dose of cyclosporin in the treatment of severe psoriasis: a randomized controlled trial. *Br. J. Dermatol.* 145(3):438-45.

Roth T., Burger A. M., Dengler W., Willmann H. and Fiebig H. H. (1999) Human tumor cell lines demonstrating the characteristics of patient tumors as useful models for anticancer drug screening. In: Fiebig H H, Burger A M (eds). Relevance of Tumor Models for Anticancer Drug Development. *Contrib. Oncol.*, 54: 145-156.

Roymans, D., and Slegers, H. (2001) Phosphaditidylinositol 3-kinases in tumor progression. *European Journal of Biochemistry* 268:487-498.

Schwecke, T., Aparicio, J. F., Molnár, I., König, A., Khaw, L. E., Haydock, S. F., Oliynyk, M., Caffrey, P., Cortés, J., Lester, J. B., Böhm, G. A., Staunton, J., and Leadlay, P. F. (1995) The biosynthetic gene cluster for the polyketide immunosuppressant rapamycin. *Proceedings of the National Academy of Sciences of the United States of America* 92: 7839-7843.

Sedrani, R., Cottens, S., Kallen, J., and Schuler, W. (1998) Chemical modifications of rapamycin: the discovery of SDZ RAD. *Transplantation Proceedings* 30: 2192-2194.

Sehgal, S. N., Baker, H., and Vézina, C. (1975) Rapamycin (AY-22,989), a new antifungal antibiotic II. Fermentation, isolation and characterization. *The Journal of Antibiotics* 28: 727-733.

Shepherd, P. R, Withers, D. J., and Siddle K. (1998) Phosphoinositide 3-kinase: the key switch mechanism in insulin signalling. *Biochemical Journal* 333: 471-490.

Smith M. B. and March J. (2001) *March's advanced organic chemistry*, 5th Ed, John Wiley and Sons Inc., UK Steiner, J. P., Hamilton, G. S., Ross, D. T., Valentine, H. L., Guo, H., Connolly, M. A., Liang, S., Ramsey, C., Li, J.-H. J., Huang, W., Howorth, P., Soni, R., Fuller, M., Sauer, H., Nowotnik, A. C., and Suzdak, P. D. (1997) Neutrophic immunophilin ligands stimulate structural and functional recovery in neurodegenerative animal models. *Proceed-* ings of the National Academy of Sciences of the United States of America 94:2019-2024.

Tang, S. J., Reis, G., Kang, H., Gingras, A.-C., Sonenberg, N., and Schuman, E. M. (2002) A rapamycin-sensitive signaling pathway contributes to long-term synaptic plasticity in the hippocampus. Proceedings of the National Academy of Sciences of the United States of America 1:467-472.

Toshima K. and Tatsuta K. (1993) Recent progress in O-glycosylation methods and its application to natural product synthesis. Chem. Rev., 93:1503-1531.

Trepanier D J, Gallant H, Legatt D F, Yatscoff R W. (1998), "Rapamycin: distribution, pharmacokinetics and therapeutic range investigations: an update". Clin Biochem. 31(5): 345-51.

Vézina, C., Kudelski, A., and Sehgal, S. N. (1975) Rapamycin (AY-22,989), a new antifungal antibiotic. I. Taxonomy of the producing streptomycete and isolation of the active principle. The Journal of Antibiotics 28: 721-726.

Volpe, D. A., Faustino, P. J., Yu, L. X., (2001) Towards standardisation of an in vitro method of drug absorption. Pharmacopeial Forum, 27, 2916-2922.

Waller, J. R., and Nicholson, M. L. (2001) Molecular mechanisms of renal allograft fibrosis. British Journal of Surgery 88:1429-1441.

Warner, L. M., Adams, L. M., Chang, J. Y., Sehgal, S. N. (1992). A modification of the in vivo mixed lymphocyte reaction and rapamycin's effect in this model. Clin. Immunol. Immunopathol. 64(3):242-7.

Yu, K., Toral-Barza, L., Discafani, C., Zhang, W. G., Skotnicki, J., Frost, P., Gibbons, J. J. (2001) mTOR, a novel target in breast cancer: the effect of CCI-779, an mTOR inhibitor, in preclinical models of breast cancer. Endocrine-Related Cancer 8:249-258.

Zhu, J., Wu J., Frizell, E., Liu, S. L., Bashey, R., Rubin, R., Norton, P., Zern, M. A. (1999). Rapamycin inhibits hepatic stellate cell proliferation in vitro and limits fibrogenesis in an in vivo model of liver fibrosis. Gastroenterology. 117 (5):1198-204.

The invention claimed is:
1. A compound according to Formula (I) below:

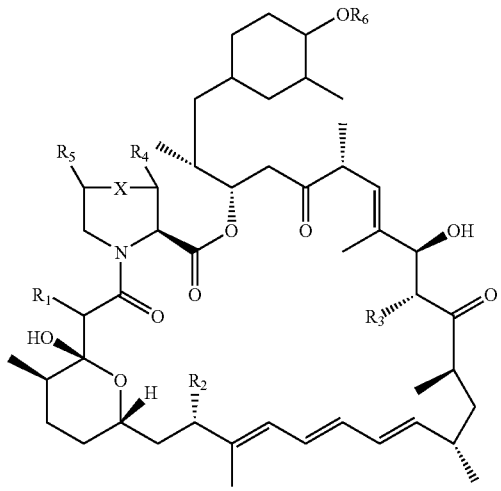

wherein:
X represents bond or $CH_2$;
$R_1$ represents a keto group or (H,H);
$R_2$ represents OH or OMe;
$R_3$ represents H, OH or OMe;
$R_4$ and $R_5$ each independently represent H or OH;
$R_6$ represents $-R_7$, $-C(O)R_7$, $-POR_{19}R_{20}$, or $Y-R_{15}$;
$R_7$ represents $-(CR_8R_9)_m(CR_{10}R_{11})_pCR_{12}R_{13}R_{14}$;
$R_8$ and $R_9$ each independently represent C1-C4 alkyl, C2-C4 alkenyl or C2-C4 alkynyl, any of which groups may optionally be substituted with $-PO(OH)_2$, $-CF_2PO(OH)_2$, $-OH$, $-COOH$ or $-NH_2$; or $R_8$ and $R_9$ each independently represent H, trifluoromethyl or F;
$R_{10}$, $R_{11}$, $R_{12}$, $R_{13}$ and $R_{14}$ each independently represent C1-C4 alkyl, C2-C4 alkenyl or C2-C4 alkynyl, any of which groups may optionally be substituted with $-PO(OH)_2$, $-CF_2PO(OH)_2$, $-OH$, $-COOH$ or $-NH_2$; or $R_{10}$, $R_{11}$, $R_{12}$, $R_{13}$ and $R_{14}$ may be independently selected from H, $-(CR_8R_9)_qNH_2$, $-(CR_8R_9)_qOH$, $CF_3$, F, COOH; or $R_{10}$ and $R_{11}$ or $R_{12}$ and $R_{13}$ or $R_{13}$ and $R_{14}$ may be taken together with the carbon to which they are joined to form a C3-C6 cycloalkyl or a 3- to 6-membered heteroalkyl ring that contains one or more heteroatoms selected from N, O and S and that is optionally, substituted with up to 5 $-(CR_8R_9)_qOH$, $-(CR_8R_9)_qNH_2$ or COOH groups;
Y=bond, $-C(O)-O-$; $-(CH_2)_2-O-C(O)-O-$;
$R_{15}$ represents

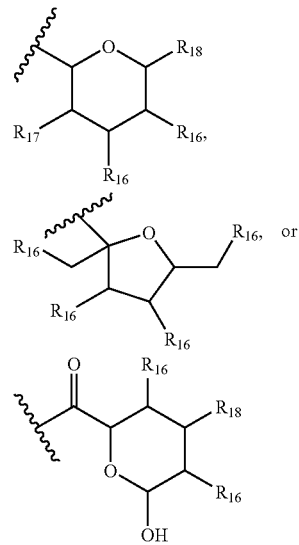

$R_{16}$ are each independently H or OH;
$R_{17}$ is independently selected from H, OH and $NH_2$;
$R_{18}$ is independently selected from H, $-CH_3$, $-CH_2OH$ and $-COOH$;
provided however that no more than 2 groups selected from $R_{16}$, $R_{17}$ and $R_{18}$ represent H or $CH_3$;
$R_{19}$ and $R_{20}$ each independently represent H or C1-C4 alkyl or $R_{19}$ and $R_{20}$ together represent $=CH_2$;
m, p and q each independently represent an integer between 0-4;
provided however that the $R_7$ moiety does not contain more than 12 carbon atoms and does contain at least one functional group selected from $-PO(OH)_2$, $-CF_2PO(OH)_2$, $-COOH$, OH or $NH_2$;
or a pharmaceutically acceptable salt thereof.

2. A compound according to claim 1 where $R_6$ represents $-R_7$.

3. A compound according to claim 1 where $R_6$ represents —C(O)$R_7$.

4. A compound according to claim 1 where $R_7$ contains 7 or fewer carbon atoms.

5. A compound according to claim 4, where $R_7$ contains 5 or fewer carbon atoms.

6. A compound according to claim 1, wherein $R_7$ contains two groups selected from —PO(OH)$_2$, —CF$_2$PO(OH)$_2$, —OH, —COOH and —NH$_2$.

7. A compound according to claim 1 wherein $R_7$ contains at least one functional group selected from —COOH, OH and NH$_2$.

8. A compound according to claim 1 wherein p represents 0 or 1.

9. A compound according to claim 1 wherein m represents 0 or 1.

10. A compound according to claim 1 wherein q represents 0, 1 or 2.

11. A compound according to claim 1 wherein $R_{11}$ represents H.

12. A compound according to claim 1, wherein $R_{12}$ represents H.

13. A compound according to claim 1, wherein $R_{13}$ represents H or OH.

14. A compound according to claim 1 where p represents 1, and $R_{10}$ represents Me, OH or CH$_2$OH.

15. A compound according to claim 1 where p represents 1 and $R_{11}$ represents Me, H or CH$_2$OH.

16. A compound according to claim 1 where m and p both represent 0, $R_{12}$ and $R_{13}$ both represent H and $R_{14}$ represents —(CR$_8$R$_9$)$_q$—OH where q=0 or 1 and $R_8$ and $R_9$ both represent H.

17. A compound according to claim 1 where p represents 1 and m represents 0, $R_{10}$ and $R_{11}$ both represent H, $R_{12}$ represents H, $R_{13}$ represents H, OH or NH$_2$ and $R_{14}$ represents —(CR$_8$R$_9$)$_q$—OH where q=0 or 1 and $R_8$ and $R_9$ both represent H.

18. A compound according to claim 1 wherein $R_6$ represents the residue derived from forming an ester with hydroxyacetic acid, 3-hydroxy-2,2-dimethylpropionic acid, 2,3-dihydroxypropionic acid, 3-hydroxy-2-hydroxymethylpropionic acid or 2,2-bis(hydroxymethyl)propionic acid.

19. A compound according to claim 1 wherein $R_6$ represents the residue derived from forming an ether with hydroxyacetic acid, 3-hydroxy-2,2-dimethylpropionic acid, 2,3-dihydroxypropionic acid, 3-hydroxy-2-hydroxymethylpropionic acid or 2,2-bis(hydroxymethyl)propionic acid.

20. A compound according to claim 1 which is 39-desmethoxy-39-methyl-40-O-[2,2-bis(hydroxymethyl)propionyl]rapamycin or a pharmaceutically acceptable salt thereof.

21. A compound according to claim 1 where $R_6$ represents —POR$_{19}$R$_{20}$.

22. A compound according to claim 21 where $R_{19}$ and $R_{20}$ both represent CH$_3$ or both represent CH$_2$CH$_3$.

23. A compound according to claim 1 where $R_6$ represents Y—$R_{15}$.

24. A compound according to claim 23 wherein $R_{15}$ group represents

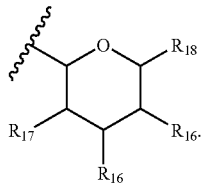

25. A compound according to claim 24 wherein $R_{15}$ is a moiety formed by forming an acetal with glucose, glucosamine, glucuronic acid or arabinose.

26. A compound according to claim 25, wherein $R_{15}$ is a moiety formed by forming an acetal with D-glucose.

27. A compound according to claim 25, wherein $R_{15}$ is a moiety formed by forming an acetal with D-glucosamine.

28. A compound according to claim 25, wherein $R_{15}$ is a moiety formed by forming an acetal with D-glucuronic acid.

29. A compound according to claim 23 wherein $R_{15}$ represents:

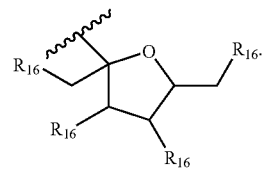

30. A compound according to claim 29, wherein $R_{15}$ is a moiety formed by forming an acetal with fructose.

31. A compound according to claim 23 wherein $R_{15}$ represents:

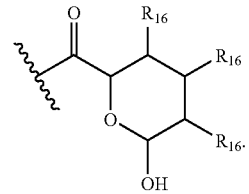

32. A compound according to claim 31, wherein $R_{15}$ is a moiety formed by forming an ester with glucuronic acid.

33. A compound according to any one of claims 23 to 32 wherein Y represents a bond.

34. A compound according to any one of claims 23 to 32 wherein Y represents —(CH$_2$)$_2$—O—C(O)—O—.

35. A compound according to any one of claims 23 to 32 wherein Y represents —C(O)—O—.

36. A pharmaceutical composition comprising a compound according to claim 1 together with one or more pharmaceutically acceptable diluents or carriers.

37. A process for preparation of a compound of formula (I) according to claim 1 which comprises:
(a) reacting a compound of formula (II):

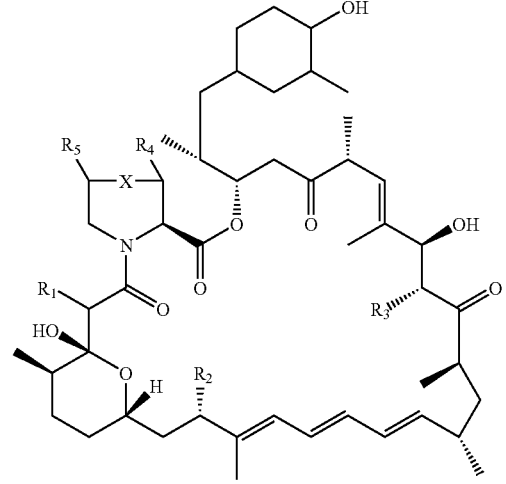

or a protected derivative thereof
with a compound of formula (III):

HO—$R_6$       (III)

or an activated derivative thereof wherein the group $R_6$ is as defined above for compounds of formula (I)

or a protected derivative thereof; or (b) converting a compound of formula (I) or a salt thereof to another compound of formula (I) or another pharmaceutically acceptable salt thereof; or (c) deprotecting a protected compound of formula (I).

38. A composition or kit of parts comprising (i) a compound according to claim 1 and (ii) one or more other therapeutically effective agent(s).

39. The composition or kit of parts of claim 38 wherein the one or more other therapeutically effective agent(s) are selected from the group of methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors, VEGF inhibitors, proteasome inhibitors, hsp90 inhibitors, azathioprine, corticosteroids, cyclophosphamide, cyclosporin A, FK506, Mycophenolate Mofetil, OKT-3, ATG, amphotericin B, flucytosine, echinocandins, griseofulvin, an imidazole and a triazole antifungal agent.

* * * * *